(12) United States Patent
Kuang

(10) Patent No.: US 11,786,176 B2
(45) Date of Patent: Oct. 17, 2023

(54) PATIENT-SPECIFIC PARAMETER ESTIMATES OF GLIOBLASTOMA MULTIFORME GROWTH DYNAMICS

(71) Applicant: Yang Kuang, Tempe, AZ (US)

(72) Inventor: Yang Kuang, Tempe, AZ (US)

(73) Assignee: Arizona Board of Regents on Behalf of Arizona State University, Tempe, AZ (US)

( * ) Notice: Subject to any disclaimer, the term of this patent is extended or adjusted under 35 U.S.C. 154(b) by 446 days.

(21) Appl. No.: 16/899,155

(22) Filed: Jun. 11, 2020

(65) Prior Publication Data

US 2020/0390387 A1 Dec. 17, 2020

Related U.S. Application Data

(60) Provisional application No. 62/859,993, filed on Jun. 11, 2019.

(51) Int. Cl.
| | | |
|---|---|---|
| *A61B 5/00* | (2006.01) | |
| *A61B 5/055* | (2006.01) | |
| *G01R 33/56* | (2006.01) | |
| *G06T 7/00* | (2017.01) | |
| *G06T 7/62* | (2017.01) | |

(Continued)

(52) U.S. Cl.
CPC .......... *A61B 5/4842* (2013.01); *A61B 5/0042* (2013.01); *A61B 5/055* (2013.01); *A61B 5/7239* (2013.01); *A61B 5/7275* (2013.01); *A61B 6/032* (2013.01); *A61B 6/037* (2013.01); *A61B 6/501* (2013.01); *G01R 33/5602* (2013.01); *G01R 33/5608* (2013.01); *G06T 7/0012* (2013.01); *G06T 7/62* (2017.01); *G06T 2207/10088* (2013.01); *G06T 2207/30096* (2013.01)

(58) Field of Classification Search
CPC ..... A61B 5/4842; A61B 5/055; A61B 5/7275; A61B 5/0042; A61B 5/7239; A61B 6/032; A61B 6/037; G01R 33/5602; G01R 33/5608; G06T 7/62; G06T 2207/30096; G06T 7/0012; G06T 2207/10088

See application file for complete search history.

(56) References Cited

U.S. PATENT DOCUMENTS

8,571,844 B2 * 10/2013 Swanson ................ G16H 50/50
  703/11
2006/0241463 A1 * 10/2006 Shau ........................ A61B 8/08
  600/455

OTHER PUBLICATIONS

Britton, Essential Mathematical Biology, Springer, 2003.
(Continued)

*Primary Examiner* — Chao Sheng
(74) *Attorney, Agent, or Firm* — POLSINELLI PC

(57) ABSTRACT

Provided herein are methods of estimating subject-specific parameters of growth dynamics of a cancer tumor in a subject having cancer. The methods can be used to personalize treatment protocols for a subject, stage the given disease in the subject, measure response to therapy, phenotype for patient selection to participate in drug trials, measure stability of an anatomical structure, or predict rate of change of the given disease. Also provided are methods of predicting growth dynamics of a cancer tumor, and computer systems and computer-implemented methods for estimating subject-specific parameters of growth dynamics of a cancer tumor in a subject having cancer.

19 Claims, 8 Drawing Sheets
(7 of 8 Drawing Sheet(s) Filed in Color)

(51) Int. Cl.
A61B 6/03 (2006.01)
A61B 6/00 (2006.01)

(56) References Cited

OTHER PUBLICATIONS

Kot, Elements of Mathematical Ecology, Cambridge University Press, 2001.
Kuang, et al., Introduction to Mathematical Oncology, 1st edition, Chapman and Hall/CRC, 2015.
Penny, et al., Statistical Parametric Mapping: The Analysis of Functional Brain Images, 1st edition, Academic Press, London, 2007.
Canosa, On a nonlinear diffusion equation describing population growth, IBM Journal of Research and Development, 17 (1973), 307-313, URL http://ieeexplore.ieee.org/ document/5391351/.
Carlson, et al., Relationship between survival and edema in malignant gliomas: role of vascular endothelial growth factor and neuronal pentraxin 2, Clinical Cancer Research, 13 (2007), 2592-2598.
Claes, et al., Diffuse glioma growth: A guerilla war, Acta Neuropathologica, 114 (2007), 443-458.
Dunbar, Traveling wave solutions of diffusive lotka-volterra equations, Journal of Mathematical Biology, 17 (1983), 11-32, URL http://link.springer.com/10.1007/BF00276112.
Eikenberry, et al., Virtual glioblastoma: Growth, migration and treatment in a three-dimensional mathematical model, Cell Proliferation, 42 (2009), 511-528.
Eisenberg, et al., A confidence building exercise in data and identifiability: Modeling cancer chemotherapy as a case study, Journal of Theoretical Biology, 431 (2017), 63-78, URL https://www.sciencedirect.com/science/article/pii/S0022519317303454?via{%}3Dihub.
Fedorov, et al., 3D Slicer as an image computing platform for the Quantitative Imaging Network, Magnetic Resonance Imaging, 1323-1341.
Fisher, The wave of advance of advantageous genes, Annals of Eugenics, 7 (1937), 355-369.
Gerlee, et al., Traveling wave analysis of a mathematical model of glioblastoma growth, Mathematical Biosciences, 276 (2016), 75-81, URL https://www.sciencedirect.com/science/article/abs/pii/S0025556416000602?via{%}3Dihub.
Gilbert, et al., Dose-dense temozolomide for newly diagnosed glioblastoma: a randomized phase III clinical trial, Journal of Clinical Oncology, 31 (2013), 4085-91.
Harley, et al., Existence of traveling wave solutions for a model of tumor invasion, SIAM Journal on Applied Dynamical Systems, 13 (2014), 366-396, URL http://epubs.siam.org/doi/10.1137/130923129.
Hoelzinger, et al., Autocrine factors that sustain glioma invasion and paracrine biology in the brain microenvironment, Journal of the National Cancer Institute, 99 (2007), 1583-1593.
Jackson, et al., Patient-specific mathematical neuro-oncology: Using a simple proliferation and invasion tumor model to inform clinical practice, Bulletin of Mathematical Biology, 77 (2015), 846-856, URL http://link. springer.com/10.1007/s11538-015-0067-7.
Kim, et al., A feasibility study of personalized prescription schemes for glioblastoma patients using a proliferation and invasion glioma model, Cancers, 9 (2017), 51, URL http://www.mdpi.com/2072-6694/9/5/51.
Kostelich, Accurate state estimation from uncertain data and models: an application of data assimilation to mathematical models of human brain tumors, Biology Direct, 6 (2011), 64, URL http://biologydirect.biomedcentral.com/articles/10.1186/1745-6150-6-64.
Madzvamuse, et al., Cross-diffusion in reaction-diffusion models: Analysis, numerics, and applications, in ECMI 2016 Progress in Industrial Mathematics at ECMI 2016 (eds. P. Quintela, P. Barral, D. Gomez, F. J. Pena, J. Rodriguez, P. Salgado and M. E. Vazquez-Mendez), Springer, 2017, 385-392.
Martirosyan et al., Mathematically modeling the biological properties of gliomas: A review, Mathematical Biosciences and Engineering, 12 (2015), 879-905, URL http://aimsciences.org/journals/displayArticlesnew.jsp?paperID=11020.
McDaniel, et al., Data assimilation in brain tumor models, in Mathematical Methods and Models in Biomedicine (eds. U. Ledzewicz, H. Schttlerand A. F. E. Kashdan), Springer, 2013, 233-262.
Murray, Glioblastoma brain tumors: estimating the time from brain tumor initiation and resolution of a patient survival anomaly after similar treatment protocols, Journal of Biological Dynamics, 6:sup2 (2012), 118-127.
Neal, et al., Discriminating sur-vival outcomes in patients with glioblastoma using a simulation-based, patient-specific response metric, PLoS ONE, 8 (2013), e51951, URL https://dx.plos.org/10.1371/journal.pone. 0051951.
Norden, et al., Glioma therapy in adults, The Neurologist, 12 (2006), 279-92, URL http://www.ncbi.nlm.nih.gov/pubmed/17122724.
Pope, et al., MR imaging correlates of survival in patients with high-grade gliomas, American Journal of Neuroradiology, 10 (2005), 2644-2474.
Sherratt, et al., A new mathematical model for avascular tumor growth, Journal of Mathematical Biology, 43 (2001), 291-312, URL http://link.springer.com/10.1007/ s002850100088.
Sherratt, Wavefront propagation in a competition equation with a new motility term modeling contact inhibition between cell populations, Proceedings of the Royal Society of London. Series A: Mathematical, Physical and Engineering Sciences, 456 (2000), 2365-2386, URL http://www.royalsocietypublishing.org/doi/10.1098/rspa.2000.0616.
Stepien, et al., A data-motivated density-dependent diffusion model of in vitro glioblastoma growth, Mathematical biosciences and engineering: MBE, 12 (2015), 1157-72, URL http://www.ncbi.nlm.nih.gov/pubmed/26775861.
Stepien, et al., Traveling waves of a go-or-grow model of glioma growth, SIAM Journal on Applied Mathematics, 78 (2018), 1778-1801, URL https://epubs. siam.org/doi/10.1137/17M1146257.
Stupp, et al., Radiotherapy plus concomitant and adjuvant temozolomide for glioblastoma, New England Journal of Medicine, 352 (2005), 987-996, URL http://www.nejm.org/doi/abs/10.1056/NEJMoa043330.
Swanson, et al., A mathematical modeling tool for predicting survival of individual patients following resection of glioblastoma: a proof of principle, British Journal of Cancer, 98 (2008), 113-119, URL http://www.nature.com/articles/6604125.
Swanson, et al., Quantifying the role of angiogenesis in malignant progression of gliomas: In silico modeling integrates imaging and histology, Cancer Research, 71 (2011), 7366-7375, URL http://www.ncbi.nlm.nih.gov/pubmed/21900399 http://www.pubmedcentral.nih.gov/articlerender.fcgi?artid=PMC3398690 http://cancerres.aacrjournals.org/cgi/doi/10.1158/0008-5472.CAN-11-1399.
Tracqui, et al., A mathematical model of glioma growth: The effect of chemotherapy on spatial-temporal growth, Cell Proliferation, 28 (1995), 17-31.
Van der Hoorn, et al., Validation of a semi-automatic co-registration of mri scans in patients with brain tumors during treatment follow-up, NMR in Biomedicine, 2 (2016), 882-889.
Watling, et al., Corticosteroid-induced magnetic resonance imaging changes in patients with recurrent malignant glioma, Journal of Clinical Oncology, 12 (1994), 1886-1889.
Woodward, et al., A math-ematical model of glioma growth: The effect of extent of surgical resection, Cell Proliferation, 29 (1996), 269-288.
Zaki, et al., Vanishing contrast enhancement in malignant glioma after corticosteroid treatment, Acta Neurochirurgica, 146 (2004), 841-845.

* cited by examiner

PATIENT-SPECIFIC PARAMETER ESTIMATES OF GLIOBLASTOMA MULTIFORME GROWTH DYNAMICS

CROSS-REFERENCE TO RELATED APPLICATIONS

This application claims the benefit of U.S. Provisional Patent Application No. 62/859,993, filed Jun. 11, 2019, the entire disclosure of which is herein incorporated by reference.

FIELD OF THE INVENTION

The present disclosure generally relates to methods for providing prognostic information relating to growth of a cancer tumor in a subject having cancer.

BACKGROUND OF THE INVENTION

Glioblastoma multiforme (GBM) is a highly aggressive primary brain cancer, with median survival time from diagnosis on the order of 15 months; long-term survival is extremely rare. The absolute survival benefit of even the most effective therapy is typically on the order of months. The highly infiltrative nature of GBMs makes recurrence nearly inevitable, even with maximal resection and aggressive adjuvant therapy, although individual tumors vary in their degree of invasiveness. Given the grim situation, mathematical modeling has been used to better understand the biophysical rules underlying GBM growth, with the ultimate goal to provide more effective, subject-specific therapy. However, currently available models of GBM growth dynamics cannot accurately model growth dynamics of GBM tumors to make patient-specific estimates of GBM growth from the limited MRI data that is typically available in clinical settings.

Therefore, there is a need for methods for determining tumor growth dynamics which are capable of accurately predicting patient-specific tumor growth, motility, and morbidity.

SUMMARY OF THE INVENTION

One aspect of the present disclosure encompasses a method of estimating subject-specific parameters of growth dynamics of a cancer tumor in a subject. The method comprises obtaining or having obtained measures of morphological features of the cancer tumor in the subject. In one aspect, the morphological features comprise a core, an invasive front, and tumor-associated tissue damage, and the measures comprising a volume of the core, a volume of the invasive front, and a volume of the tumor-associated tissue damage. The method further comprises quantifying the measures by deriving idealized radii representing a radius of the core, a radius to the invasive front, and a radius to an outer edge of tumor-associated tissue damage; obtaining an approximate wave profile of a traveling wave solution generated using a reaction-diffusion model of tumor growth; and estimating subject-specific parameters by fitting the approximate wave profile to a tumor profile derived from the quantified measures. The growth dynamics comprise motility, birth, and death dynamics of the tumor.

The morphological measures of the cancer tumor can be obtained at a single time point or at two consecutive time points. The idealized radii can be quantified by approximating the tumor and the morphological features of the tumor as a sphere, and identifying radii of a sphere representing the inner core, a sphere representing the invasive front, and a sphere representing the outer edge of tumor-associated tissue damage.

The morphological measures of the cancer tumor can be obtained from clinical imaging data. In some aspects, the clinical imaging data is magnetic resonance imaging (MRI).

The reaction-diffusion model of tumor growth can be a three-parameter reaction-diffusion model of tumor growth derived from the Fisher-Kolmogorov equation. In some aspects, the reaction-diffusion model of tumor growth is the system of reaction diffusion equations (2.8a) and (2.8b), and the motility can be diffusion coefficient (D), birth dynamics can be intrinsic tumor cell growth rate (p), and death dynamics can be death rate (k) of the tumor. The model can be used to obtain an approximate wave profile of a traveling wave solution that mimics tumor progression, with the traveling wave speed being an indicator of speed of tumor progression. Fitting the approximate wave profile to a tumor profile can comprise fitting the approximate wave profile to a tumor image wave profile derived from the radius of the inner core, radius to the invasive front, and radius to the outer edge of tumor-associated tissue damage.

In some aspects, the tumor is glioblastoma multiforme (GBM). When the tumor is GBM, the inner core is inner necrotic core, the invasive front correlates with high blood vessel density, and the outer edge of tumor-associated tissue damage is the outer edge of tumor-associated edema. Further, when the tumor is GBM, the clinical imaging data comprises MR images, and MR images are T1-weighted and T2-weighted MR images of the tumor. Clinical MRI data can comprise a single MR image or an MRI sequence taken at a single time point. Clinical MRI data can also comprise a single MR image or an MRI sequence taken at a single time point prior to surgery or images acquired at two consecutive time points prior to surgery.

The method can further comprise using the estimated parameters of growth dynamics of the tumor to estimate time of initiation of the tumor. The method can also further comprise using the estimated parameters of growth dynamics of the tumor to estimate future growth of the tumor.

Another aspect of the present disclosure encompasses a method of determining a personalized treatment protocol for a subject having a cancer tumor. The method comprises estimating subject-specific parameters of growth dynamics of a cancer tumor in the subject using the method described above. The method further comprising assigning a treatment protocol based on the estimated subject-specific parameters of growth dynamics of the cancer tumor. The method can further comprise further obtaining or having obtained descriptive information relating to the subject, and assigning the treatment protocol based on the estimated subject-specific parameters and the descriptive information, the descriptive information comprising one or more data elements.

Yet another aspect of the present disclosure encompasses a method of monitoring the therapeutic effect of a cancer treatment protocol in a subject. The method comprises estimating a first set of patient-specific parameters of growth dynamics of a cancer tumor in the patient using a method described in this section above, and administering a cancer treatment. The method further comprises estimating a first set of patient-specific parameters of growth dynamics of a cancer tumor in the patient, and comparing the second set of patient-specific parameters to the first set of patient-specific parameters. Maintenance of the second set of patient-specific parameters, or a change of the second set of patient-specific parameters when compared to the first set of patient-specific parameters, is indicative of the therapeutic effect of the cancer treatment in the subject. The method can further comprise obtaining or having obtained descriptive information relating to the subject, the descriptive information comprising one or more data elements.

Another aspect of the present disclosure encompasses a computer-implemented method for estimating subject-specific parameters of growth dynamics of a cancer tumor in a subject having a cancer tumor. The method comprises providing a computer system having at least one processor and associated memory comprising an approximate wave profile of a traveling wave solution obtained using a reaction-diffusion model of tumor growth.

The computer system comprises instructions to quantify morphological measures of the cancer tumor in the subject, the morphological features comprising a core, an invasive front, and tumor-associated tissue damage, and the measures comprising a volume of the core, a volume of the invasive front, and a volume of the tumor-associated tissue damage. The computer also comprises instructions to estimate the subject-specific parameters by fitting an approximate wave profile of a traveling wave solution to a tumor profile derived from the quantified measures. The approximate wave profile is generated using a reaction-diffusion model of tumor growth.

The computer-implemented method further comprises inputting the morphological measures of the cancer tumor in the subject. The measures comprise measures of the inner core, the invasive front, and the maximum extent of tumor-associated tissue damage. Further, the computer-implemented method comprises processing the morphological measures to quantify the morphological measures of the cancer tumor in the subject; processing the traveling solution profile of the reaction-diffusion model to fit the solution profile to the quantified measures; and computing the subject-specific parameters of growth dynamics of the cancer tumor from the fitted traveling solution profile. The computer-implemented method can further comprise inputting descriptive information relating to the subject, the descriptive information comprising one or more data elements Another aspect of the present disclosure encompasses at least one non-transitory computer readable medium. The medium stores instructions which, when executed, cause the at least one processor to receive imaging data from an imaging device. The imaging data can be obtained from one or more images provided by the imaging device, such as images of the tumor and/or tumor-associated tissue damage. The imaging data comprises measures of morphological features of a cancer tumor in a subject, the morphological features comprising a core and an invasive front of the front of the tumor, and tumor-associated tissue damage thereof, and the measures comprising a volume of the core, a volume of the invasive front, and a volume of the tumor-associated tissue damage. The instructions can further cause the at least one processor to quantify the measures by deriving idealized radii representing a radius of the core, a radius to the invasive front, and a radius to an outer edge of tumor-associated tissue damage, and to estimate the subject-specific parameters by fitting an approximate wave profile of a traveling wave solution to a tumor profile derived from the measures. The approximate wave profile is generated using a reaction-diffusion model of tumor growth. The imaging data can be determined from one or more images of the tumor and/or tumor-associated tissue damage. The medium can further comprise instructions, which when executed by the at least one processor, cause the at least one processor to display subject-specific parameters of tumor growth dynamics, wherein the growth dynamics comprise motility, birth, and death dynamics of the tumor. Further, the medium can also comprise instructions, which when executed by the at least one processor cause the at least one processor to generate a report of the subject-specific parameters of tumor growth dynamics.

Yet another aspect of the present disclosure encompasses a system for estimating subject-specific parameters of growth dynamics of a cancer tumor in a subject. The system comprises an imaging device for obtaining morphological measures of the cancer tumor in the subject, the measures comprising measures of the inner core, the invasive front, and the maximum extent of tumor-associated tissue damage. The measures comprise a volume of the core, a volume of the invasive front, and a volume of the tumor-associated tissue damage.

The system further comprises a processor. The processor is configured for quantifying the measures by deriving idealized radii representing the radius of the inner core, the radius to the invasive front, and the radius to the outer edge of tumor-associated tissue damage. The processor is also configured for estimating the subject-specific parameters by fitting an approximate wave profile of a traveling wave solution to a tumor profile derived from the quantified measures. The approximate wave profile is generated using a reaction-diffusion model of tumor growth.

The system also comprises an interface unit to display the subject-specific parameters of growth dynamics, wherein the growth dynamics comprise motility, birth, and death dynamics of the tumor. The processor can further be configured to obtain descriptive information relating to the subject, the descriptive information comprising one or more data elements.

Another aspect of the present disclosure encompasses a

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

The present disclosure encompasses a method of estimating subject-specific parameters of growth dynamics of a cancer tumor in a subject having cancer, and systems and computer programs to implement the method. The method comprises use of a mathematical model of tumor growth dynamics with explicit motility, birth, and death processes. The method can be used for determining a personalized treatment protocol for the subject, staging the tumor in the subject, measuring response of the tumor to therapy, phenotyping the tumor for subject selection to participate in drug trials, measuring stability of the tumor, or predicting rate of change of the tumor.

I. Methods

Figure 7:
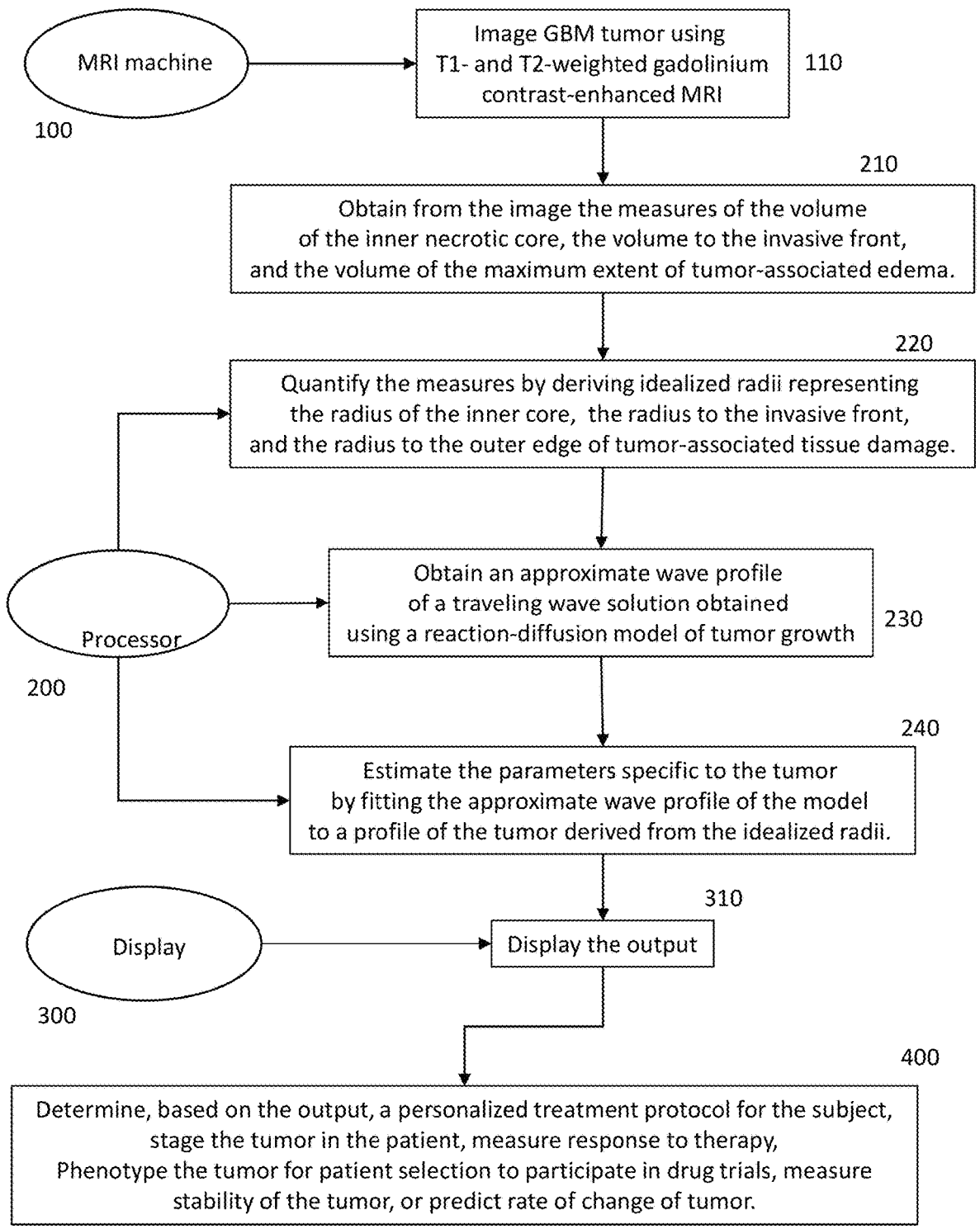
FIG. 7. Flow diagram illustrating an aspect of a system for performing steps of a method for estimating subject-specific parameters of growth dynamics of a cancer tumor in a subject.

One aspect of the present disclosure encompasses a method of estimating subject-specific parameters of growth dynamics of a cancer tumor in a subject. An aspect of the method of the disclosure when used in a system for estimating subject-specific parameters of growth dynamics of the cancer tumor is shown in FIG. 7.

A tumor can be any abnormal mass of tissue, the growth of which exceeds and is uncoordinated with that of the normal tissues, and persists in the same excessive manner after cessation of the stimuli, which evoked the change. Although the appearance of tumors can vary based on the subject, the cancer, the stage of development of the cancer and tumor, and the tissue in which the cancer is developing, among others, the gross appearance of a tumor is generally round, oval, or coarsely nodular, and well circumscribed. Cancers and cancer tumors can be as described in Section I(b) below.

A tumor generally comprises an inner core, an invasive front normally with rapid cell proliferation, and tumor-associated tissue damage surrounding the tumor front. The inner core can be formed of necrotic cells or tissue, the invasive front can be associated with high blood vessel density, and tumor-associated tissue damage can be tumor-associated edema. The method comprises obtaining measures of the inner core, the invasive front, and the maximum extent of tumor-associated tissue damage. The measures comprise the volume of the core, the volume of the invasive front volume, and the volume of the tumor-associated tissue damage.

In some aspects, the morphological measures of the cancer tumor are obtained from clinical imaging data. For instance, the imaging data can be obtained from an MRI image stack by manually or computationally deriving each volume from the image stack. Stacks are a set of sequential images from cross-sectional modalities (e.g. CT/MRI) or time-resolved modalities (e.g. DSA). In some aspects, the image stacks are initially registered to a standard brain space, and the total necrotic core volumes, enhancing rim volumes, and tumor-associated edema volumes are determined from segmentation of the tumor image. Methods of imaging a tumor can be as described in Section 1(c) below.

The morphological measures of the cancer tumor can be obtained at a single time point. Alternatively, the morphological measures can be obtained at two consecutive time points. For instance, when the morphological measures are obtained at two consecutive time points, the second morphological measures can be obtained 1 day, 1 week, 2 weeks, 1 month, 2, months, 3 months, 4 months, 5 months, 6 months, 7 months, 8 months, 9 months, 10 months, 11 months, or 1 year after the first morphological measures are obtained. In some aspects, when the morphological measures are obtained at two consecutive time points, the second morphological measures are obtained about one month after the first morphological measures are obtained. In some aspects, when the morphological measures are obtained at two consecutive time points, the second morphological measures are obtained at least one month after the first morphological measures are obtained.

The methods further comprise quantifying the volumes of the core, the enhancing rim, and the tumor-associated edema by deriving idealized radii representing the radius of the inner core, the radius to the invasive front, and the radius to the outer edge of tumor-associated tissue damage. Methods of quantifying the volumes of the core, the volume of the invasive front volume, and the volume of the tumor-associated tissue damage can and will vary depending on the morphological features measured, the method of measuring the morphological features, the cancer tumor, and the stage of the cancer tumor among others, and are known or can be determined by an individual of skill in the art. In some aspects, volumes can be measured by approximating the tumor and the morphological features of the tumor as a sphere, and identifying radii of the inner core, the invasive front, and the outer edge of tumor-associated tissue damage.

The model can be a system of reaction-diffusion equations. Reaction-diffusion systems are mathematical models which correspond to several physical phenomena. The models can describe dynamical processes to describe the spreading of biological populations. In most biological applications of reaction-diffusion models, solutions take the form of traveling waves. In some aspects, the equations of the model are variants of the Fisher-Kolmogorov equation. In some aspects, the model is the system of reaction diffusion equations (2.8a) and (2.8b) which describes the growth of tumor cells, as shown and derived in the Examples. In one aspect, when the model is the system of reaction diffusion equations (2.8a) and (2.8b), the motility is diffusion coefficient (D), birth dynamics is intrinsic tumor cell growth rate (p), and death dynamics is death rate (k) of the tumor. In some aspects, D ranges from about 0.01 to about 2 mm$^2$/day, from about 0.05 to about 1.5 mm$^2$/day, or from about 0.1 to about 1.5 mm$^2$/day. In some aspects, ρ ranges from about 0.1 to about 0.5 day-1, or from about 0.1 to about 0.5 day-1. In some aspects, k ranges from about 0.01 to about 1 day$^{-1}$, or from about 0.05 to about 0.8 day$^{-1}$.

Figure 3A:
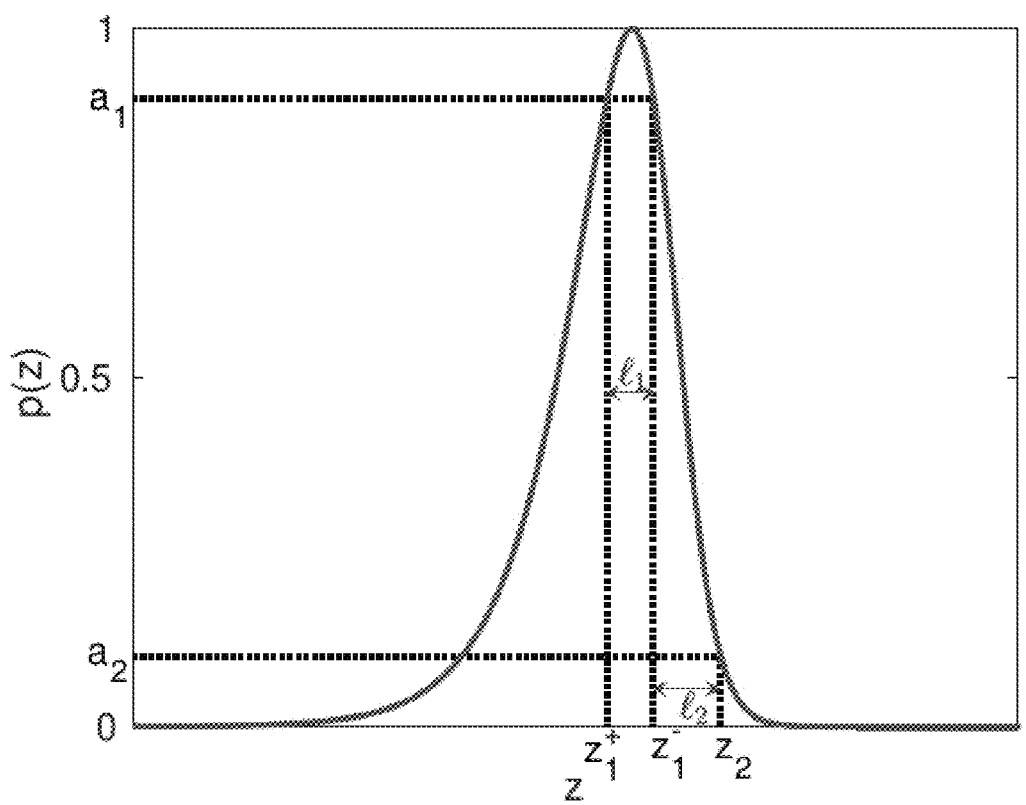
FIG. 3A. Normalized wave profile generated by the model in the z coordinate.

The model is used to obtain an approximate wave profile of a traveling wave solution that mimics tumor progression, with the traveling wave speed being an indicator of speed of tumor progression. The approximate wave profile can be as shown in FIG. 3A. According to the methods, the subject-specific parameters are then estimated by fitting the approximate wave profile to a tumor image wave profile (FIG. 3B) derived from the quantified radius of the inner core, radius to the invasive front, and radius to the outer edge of tumor-associated tissue damage.

The ability to model the growth dynamics comprising motility, birth, and death dynamics of the tumor can contribute to better predictive tools for designing tumor therapy in the clinic. Such information can be used to determine a personalized treatment protocol for the subject, staging the tumor in the subject, measuring response of the tumor to therapy, phenotyping the tumor for subject selection to participate in drug trials, measuring stability of the tumor, or predicting rate of change of the tumor. The growth dynamics are the rates of motility, birth, and death of the tumor. Methods of treatment and treatment protocols can be as described in Section I(e) below.

Another aspect of the present disclosure encompasses a method of determining a personalized treatment protocol for a subject having a cancer tumor. The method comprises estimating subject-specific parameters of growth dynamics of a cancer tumor in the subject using the method described above. The method further comprises assigning a treatment protocol based on the estimated subject-specific parameters of growth dynamics of the cancer tumor.

Yet another aspect of the present disclosure encompasses a method of monitoring the therapeutic effect of a cancer treatment protocol in a subject. The method comprises estimating a first set of patient-specific parameters of growth dynamics of a cancer tumor in the patient using a method described in this section above, and administering a cancer treatment. The method further comprises estimating a first set of patient-specific parameters of growth dynamics of a cancer tumor in the patient, and comparing the second set of patient-specific parameters to the first set of patient-specific parameters. Maintenance of the second set of patient-specific parameters, or a change of the second set of patient-specific parameters when compared to the first set of patient-specific parameters, is indicative of the therapeutic effect of the cancer treatment in the subject.

(a) Subject

A subject can be any subject having a tumor. The subject can be a human, a livestock animal, a companion animal, a lab animal, or a zoological animal. In one aspect, the subject is a rodent, e.g. a mouse, a rat, a guinea pig, etc. Non-limiting examples of suitable livestock animals may include pigs, cows, horses, goats, sheep, llamas and alpacas. Non-limiting examples of companion animals may include pets such as dogs, cats, rabbits, and birds. As used herein, a "zoological animal" refers to an animal that may be found in a zoo. Such animals may include non-human primates, large cats, wolves, and bears. Non-limiting examples of a laboratory animal may include rodents, canines, felines, and non-human primates. In some aspects, the subject is a human subject. In some aspects, the subject is a human subject having a GBM tumor.

(b) Cancer

A method of the disclosure may be used to estimate the growth dynamics of a tumor derived from a neoplasm or a cancer. "Neoplasm" is any tissue, or cell thereof, characterized by abnormal growth as a result of excessive cell division. The neoplasm can be malignant or benign, the cancer can be primary or metastatic; the neoplasm or cancer can be early stage or late stage. Non-limiting examples of neoplasms or cancers that can be treated or detected include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), breast cancer, bronchial adeno-mas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, glioma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sézary syndrome, skin cancers (non-melanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-Cell lymphoma (cutaneous), testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), unknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macro-globulinemia, and Wilms tumor (childhood).

In some aspects, the cancer tumor is a neural cancer, such as neuroblastoma and glioma. Neuroblastoma is initiated in the embryo at a moment when the nervous system (NS) is in full expansion and occasionally genomic damage can lead to neoplasia. Glioma, to the contrary, occurs in the adult brain supposed to be mostly in a postmitotic state. In some aspects, the tumor is a neuroblastoma. In other aspects, the cancer tumor is a glioblastoma (GBM).

(c) Imaging

The morphological measures of the cancer tumor are obtained from clinical imaging data. As such, a method of the disclosure includes obtaining or having obtained a clinical image of the tumor, and deriving measures of the morphological features from the images. Methods used to image a tumor can and will vary depending on the tumor, the tissue in which the tumor is growing, the various parts of the tumor that are to be enhanced or highlighted, the stage of development of the tumor, among others. Non-limiting examples of imaging techniques suitable for use in imaging cancers and tumors include X-ray imaging, Computed Tomography (CT) scans, Molecular and Nuclear Imaging (PET and SPECT), radiography, Ultrasound, and Magnetic Resonance Imaging (MRI). Often, a combination of these methods can be used to visualize different parts of a tumor. Further, each of the imaging techniques can be adapted, modified, or customized and combined with other techniques or imaging agents to highlight morphological features of the tumor and tissue surrounding the tumor.

Imaging techniques can be used with imaging agents to make things visible. As used herein, an "imaging agent" is any type of agent, which, when administered to a tumor or a subject having the tumor, renders the tumor and various features of the tumor detectable. An imaging agent may also be toxic to cells or cytotoxic. Accordingly, an imaging agent may also be a therapeutic agent or cytotoxic agent. In general, imaging agents may include luminescent molecules, chemiluminescent molecules, fluorochromes, fluorophores, fluorescent quenching agents, colored molecules, radioisotopes, radionuclides, cintillants, massive labels such as a metal atom (for detecting via mass changes), biotin, avidin, streptavidin, protein A, protein G, antibodies or fragments thereof, Grb2, polyhistidine, $Ni^{2+}$, Flag tags, myc tags, heavy metals, enzymes, alkaline phosphatase, peroxidase, luciferase, electron donors/acceptors, acridinium esters, and colorimetric substrates. The skilled artisan would readily recognize other useful imaging agents that are not mentioned above which may be employed in the operation of the present invention.

An imaging agent emits a signal that can be detected by a signal transducing machine. In some cases, the imaging agent can emit a signal spontaneously, such as when the imaging agent is a radionuclide. In other cases, the imaging agent emits a signal as a result of being stimulated by an external field such as when the imaging agent is a relaxivity metal. Examples of signals include, without limitation, gamma rays, X-rays, visible light, infrared energy, and radiowaves. Examples of signal transducing machines include, without limitation, gamma cameras including SPECT/CT devices, PET scanners, fluorimeters, and Magnetic Resonance Imaging (MRI) machines. As such, the imaging agent comprises a label that can be detected using magnetic resonance imaging, scintigraphic imaging, ultrasound, or fluorescence.

Suitable fluorophores include, but are not limited to, fluorescein isothiocyante (FITC), fluorescein thiosemicarbazide, rhodamine, Texas Red, CyDyes (e.g., Cy3, Cy5, Cy5.5), Alexa Fluors (e.g., Alexa488, Alexa555, Alexa594; Alexa647), near infrared (NIR) (700-900 nm) fluorescent dyes, and carbocyanine and aminostyryl dyes. $B_{12}$ or an analog thereof can be labeled for fluorescence detection by labeling the agent with a fluorophore using techniques well known in the art (see, e.g., Lohse et al., Bioconj Chem 8:503-509 (1997)). For example, many known dyes are capable of being coupled to $NH_2$-terminal groups. Alternatively, a fluorochrome such as fluorescein may be bound to a lysine residue of a peptide linker.

A radionuclide may be a γ-emitting radionuclide, Auger-emitting radionuclide, β-emitting radionuclide, an α-emitting radionuclide, or a positron-emitting radionuclide. A radionuclide may be an imaging agent and/or a therapeutic agent. Non-limiting examples of suitable radionuclides may include carbon-11, nitrogen-13, oxygen-15, fluorine-18, fluorodeoxyglucose-18, phosphorous-32, scandium-47, copper-64, 65 and 67, gallium-67 and 68, bromine-75, 77 and 80m, rubidium-82, strontium-89, zirconium-89, yttrium-86 and 90, ruthenium-95, 97,103 and 105, rhenium-99m, 101, 105, 186 and 188, technetium-99m, rhodium-105, mercury-107, palladium-109, indium-111, silver-111, indium-113m, lanthanide-114m, tin-117m, tellurium-121m, 122m and 125m, iodine-122, 123, 124, 125, 126, 131 and 133, praseodymium-142, promethium-149, samarium-153, gadolinium-159, thulium-165, 167 and 168, dysprosium-165, holmium-166, lutetium-177, rhenium-186 and 188, iridium-192, platinum-193 and 195m, gold-199, thallium-201, titanium-201, astatine-211, bismuth-212 and 213, lead-212, radium-223, actinium-225, and nitride or oxide forms derived therefrom.

A variety of metal ions may be used as an imaging agent. For instance, the metal ion may be a calcium ion, scandium ion, titanium ion, vanadium ion, chromium ion, manganese ion, iron ion, cobalt ion, nickel ion, copper ion, zinc ion, gallium ion, germanium ion, arsenic ion, selenium ion, bromine ion, krypton ion, rubidium ion, strontium ion, yttrium ion, zirconium ion, niobium ion, molybdenum ion, technetium ion, ruthenium ion, rhodium ion, palladium ion, silver ion, cadmium ion, indium ion, tin ion, antimony ion, tellurium ion, iodine ion, xenon ion, cesium ion, barium ion, lanthanum ion, hafnium ion, tantalum ion, tungsten ion, rhenium ion, osmium ion, iridium ion, platinum ion, gold ion, mercury ion, thallium ion, lead ion, bismuth ion, francium ion, radium ion, actinium ion, cerium ion, praseodymium ion, neodymium ion, promethium ion, samarium ion, europium ion, gadolinium ion, terbium ion, dysprosium ion, holmium ion, erbium ion, thulium ion, ytterbium ion, lutetium ion, thorium ion, protactinium ion, uranium ion, *neptunium* ion, plutonium ion, americium ion, curium ion, berkelium ion, californium ion, einsteinium ion, fermium ion, mendelevium ion, nobelium ion, or lawrencium ion.

The metal ion may be a metal ion in the form of +1, +2, or +3 oxidation states. For instance, non-limiting examples include $Ba^{2+}$, $Bi^{3+}$, Cs+, $Ca^{2+}$, $Cr^{2+}$, $Cr^{3+}$, $Cr^{6+}$, $Co^{2+}$, $Co^{3+}$, $Cu^+$, $Cu^{2+}$, $Cu^{3+}$, $Ga^{3+}$, $Gd^{3+}$, $Au^+$, $Au^{3+}$, $Fe^{2+}$, $Fe^{3+}$, $F^{3+}$, $Pb^{2+}$, $Mn^{2+}$, $Mn^{3+}$, $Mn^{4+}$, $Mn^{7+}$, $Hg^{2+}$, $Ni^{2+}$, $Ni^{3+}$, $Ag+$, $Sr^{2+}$, $Sn^{2+}$, $Sn^{4+}$, and $Zn^{2+}$. The metal ion may be part of a metal oxide. For instance, non-limiting examples of metal oxides may include iron oxide, manganese oxide, or gadolinium oxide. Additional examples may include magnetite, maghemite, or a combination thereof.

The selection of an imaging agent can differ between imaging techniques. For instance, Gadolinium is a contrast agent that may be given during MRI scans; it highlights areas of tumor or inflammation. Sometimes the gadolinium is given midway through the MRI scan by injection into a vein. PET and nuclear medicine requires use of radioactive contrast agents (radiopharmaceuticals) to obtain images. Some agents used for PET imaging provide information about tissue metabolism or some other specific molecular activity. Non-limiting examples of radiopharmaceuticals used in PET and nuclear medicine include 64Cu-ATSM (64Cu diacetyl-bis(N4-methylthiosemicarbazone)), FDG (18F-fluorodeoxyglucose, 18F-fluoride, FLT (3'-deoxy-3'-[18F]fluorothymidine, FMISO (18F-fluoromisonidazole), Gallium, Technetium-99m, and Thallium. Non-limiting examples of X-ray imaging agents include Barium, Gastrografin, and Iodine contrast agents.

(d) GBM

In some aspects, the tumor is a GBM tumor. GBMs morphologically typically appear (at least at initial diagnosis) as roughly spherical but highly heterogeneous masses that often exhibit a (crudely speaking) three-layer structure. Within the tumor there is usually extensive cell necrosis, often accompanied by tumor cells, and a cystic component as well. An outer invasive front cytologically typified by proliferating cells that then infiltrate into surrounding brain tissue. The surrounding brain tissue is generally seen to be edematous due to vasogenic edema. Prior statistical analyses have found that edema is a prognostic indicator of patient survival, but the relationship is complex and appears to be mediated by the expression of vascular endothelial growth factor and the activity of related angiogenic genes and various autocrine factors.

In some aspects, clinical images of GBM tumors are obtained using computed tomography (CT scans). CT scan images offer a relatively high degree of confidence for the diagnosis of glioblastoma multiforme (GBM). However, some lesions may mimic GBM, such as space-occupying lesions including brain abscess, infarct with hemorrhagic transformation, and neoplasms of a lower grade than that of GBM. In addition, some types of demyelinating lesions (e.g., giant multiple sclerosis plaques) may mimic GBM, and the multifocal form of GBM may be indistinguishable from diffuse multiple sclerosis. Non-enhanced CT scan findings may include a heterogeneous poorly marginated mass; internal areas of low or fluid attenuation that are the foci of necrosis; internal areas of high attenuation that are the foci of hemorrhage or, rarely, calcifications; and a significant mass effect and edema (vasogenic distribution of the edema). Enhanced CT scans include significant enhancement of findings such as irregularity and inhomogeneity; possible ring enhancement; possible, but uncommon, solid enhancement; possible little enhancement possible in diffuse forms.

In some aspects, images of the GBM tumor are obtained using nuclear imaging. Positron emission tomography (PET) scanning is a useful adjunct to the evaluation of GBM, particularly after resection. In this setting, differentiation of residual or recurrent tumor and postoperative edema or scarring is often difficult on MRIs or CT scans. PET scanning with $^{18}$-fluorodeoxyglucose (FDG) is useful in cases of active tumor, which shows high metabolic activity and glucose utilization, and in cases of simple postoperative edema or scars, which usually have no increased activity. In the setting of resection for known tumor, the finding of increased tracer uptake at the surgical site is a reliable indicator of recurrent disease. However, after radiotherapy, increased activity may be seen at the surgical site without tumor recurrence. False-positive findings occur after radiation therapy, when active granulation tissue can metabolize FDG, which may limit the sensitivity of the study in this setting. An epileptogenic focus near the surgical site may show increased uptake on PET scanning, particularly if epileptic activity is high.

In some aspects, images of the GBM tumor are obtained using angiography. Angiographic findings associated with GBM include the following: hypervascular mass with tumor blush; prominent feeding and draining vessels, as well as arteriovenous shunting (this may mimic an arteriovenous malformation); aberrant vessels and vascular pooling and stasis (common); and mass effect, which is seen as displacement of vessels. Angiography has low specificity for the diagnosis of GBM. Although images may show vascular displacement on the basis of the mass effect of the tumor, virtually any other space-occupying lesion may have similar findings. In addition, the hypervascularity of GBM may mimic vascular malformations. Thus, any space-occupying lesion or vascular malformation with hypervascularity may cause a false-positive finding. Small tumors or those with a high infiltrative component and little or no vascular displacement may cause a false-negative finding.

In some aspects, images of the GBM tumor are obtained using MRI. MRI has a high degree of confidence in the diagnosis of GBM and is widely used for identifying location and size of brain tumors. In fact, it can have the highest degree of confidence of any imaging modality. Some lesions, mainly space-occupying lesions with hemorrhagic components, may mimic GBM on MRIs. These include abscesses and infarcts. Conventional MRI is limited in its ability to determine type and grade of brain tumors, but more advanced MRI techniques, such as perfusion-weighted imaging, may provide potentially more physiologic information. MRI findings demonstrate a heterogeneous mass that is generally of low signal intensity on T1-weighted images and high signal intensity on T2-weighted images. There are internal cystic areas, internal flow voids representing prominent vessels, internal areas of high signal intensity on T1 (hemorrhagic foci), neovascularity, necrotic foci, significant peritumoral vasogenic edema, and significant mass effect. Irregular but intense enhancement after the administration of gadolinium-based contrast material (same pattern as with enhanced CT scanning) is also found, as are metastatic foci of intracerebral metastasis that are common with GBM. In one alternative of the aspects, the GBM tumor and the surrounding tissue damage is imaged using gadolinium contrast-enhanced MRI. In one aspect, the invasive front is the contrast-enhancing rim ($R_1$) imaged on T1-weighted gadolinium, and the maximum extent of tumor damage is tumor-associated tissue edema imaged on T2-weighted or T2-FLAIR MRI contrast-enhanced MRI.

When the tumor is a GBM tumor, the inner core is the inner necrotic core of the GBM tumor, the invasive front can correlate with high blood vessel density and rapid cell proliferation, and the maximum extent of tumor-associated tissue damage is the radius to the outer edge of tumor-associated edema. When the GBM is imaged using MRI, the invasive front appears as contrast-enhancing on T1-weighted gadolinium contrast-enhanced MRI, and the maximum extent of tumor-associated tissue damage can be seen to be edematous on T2-weighted or T2-FLAIR MRI.

(e) Treatment

As explained in Section I above, methods of the invention can be used to determine a personalized treatment protocol for the subject and measuring response of the tumor to therapy. The growth dynamics are the rates of motility, birth, and death of the tumor. Methods of treating cancer can include surgical removal of the tumor. Alternatively, or in combination with surgical intervention for treating a tumor, treatment can further comprise the use of therapeutic agents.

Methods and combination therapies described herein may be used to treat any cancer neoplasm or tumor. The neoplasm may be malignant or benign; the cancer may be primary or metastatic; and the neoplasm or cancer may be early stage or late stage.

Any therapeutic antineoplastic agent with activity against a cancer tumor can be used in a method of the invention. A "therapeutic agent" is any compound known in the art that is used in the detection, diagnosis, or treatment of a condition or disease. Such compounds may be naturally-occurring, modified, or synthetic. Non-limiting examples of therapeutic agents may include drugs, therapeutic compounds, genetic materials, metals (such as radioactive and non-radioactive isotopes), proteins, peptides, carbohydrates, lipids, steroids, nucleic acid-based materials or derivatives, analogues, or combinations thereof in their native form or derivatized with hydrophobic or charged moieties to enhance incorporation or adsorption into a cell. Such therapeutic agents may be water soluble or may be hydrophobic. Non-limiting examples of therapeutic agents may include immune-related agents, thyroid agents, respiratory products, antineoplastic agents, anti-helmintics, anti-malarials, mitotic inhibitors, hormones, anti-protozoans, anti-tuberculars, cardiovascular products, blood products, biological response modifiers, anti-fungal agents, vitamins, peptides, anti-allergic agents, anti-coagulation agents, circulatory drugs, metabolic potentiators, anti-virals, anti-anginals, antibiotics, anti-inflammatories, anti-rheumatics, narcotics, cardiac glycosides, neuromuscular blockers, sedatives, local anesthetics, general anesthetics, or radioactive or non-radioactive atoms or ions. Non-limiting examples of therapeutic agents are described below.

A therapeutic agent of the invention may be a small molecule therapeutic, a therapeutic antibody, a therapeutic nucleic acid, or a chemotherapeutic agent. Non-limiting examples of therapeutic antibodies may include muromomab, abciximab, rituximab, daclizumab, basiliximab, palivizumab, infliximab, trastuzumab, etanercept, gemtuzumab, alemtuzumab, ibritomomab, adalimumab, alefacept, omalizumab, tositumomab, efalizumab, cetuximab, bevacizumab, natalizumab, ranibizumab, panitumumab, eculizumab, and certolizumab. A representative therapeutic nucleic acid may encode a polypeptide having an ability to induce an immune response and/or an anti-angiogenic response in vivo. Representative therapeutic proteins with immunostimulatory effects include, but are not limited to, cytokines (e.g., an interleukin (IL) such as IL2, IL4, IL7, IL12, interferons, granulocyte-macrophage colony-stimulating factor (GM-CSF), tumor necrosis factor alpha (TNF-α)), immunomodulatory cell surface proteins (e.g., human leukocyte antigen (HLA proteins), co-stimulatory molecules, and tumor-associated antigens. See Kirk & Mule, 2000; Mackensen et al., 1997; Walther & Stein, 1999; and references cited therein. Representative proteins with anti-angiogenic activities that can be used in accordance with the presently disclosed subject matter include: thrombospondin I (Kosfeld & Frazier, 1993; Tolsma et al., 1993; Dameron et al., 1994), metallospondin proteins (Carpizo & Iruela-Arispe, 2000), class I interferons (Albini et al., 2000), IL12 (Voest et al., 1995), protamine (Ingber et al., 1990), angiostatin (O'Reilly et al., 1994), laminin (Sakamoto et al., 1991), endostatin (O'Reilly et al., 1997), and a prolactin fragment (Clapp et al., 1993). In addition, several anti-angiogenic peptides have been isolated from these proteins (Maione et al., 1990; Eijan et al., 1991; Woltering et al., 1991). Representative proteins with both immunostimulatory and anti-angiogenic activities may include IL12, interferon-γ, or a chemokine. Other therapeutic nucleic acids that may be useful for cancer therapy include, but are not limited to, nucleic acid sequences encoding tumor suppressor gene products/antigens, antimetabolites, suicide gene products, and combinations thereof.

A chemotherapeutic agent refers to a chemical compound that is useful in the treatment of cancer. The compound may be a cytotoxic agent that affects rapidly dividing cells in general, or it may be a targeted therapeutic agent that affects the deregulated proteins of cancer cells. A cytotoxic agent is any naturally-occurring, modified, or synthetic compound that is toxic to tumor cells. Such agents are useful in the treatment of neoplasms, and in the treatment of other symptoms or diseases characterized by cell proliferation or a hyperactive cell population. The chemotherapeutic agent may be an alkylating agent, an anti-metabolite, an anti-tumor antibiotic, an anti-cytoskeletal agent, a topoisomerase inhibitor, an anti-hormonal agent, a targeted therapeutic agent, a photodynamic therapeutic agent, or a combination thereof.

Non-limiting examples of suitable alkylating agents may include altretamine, benzodopa, busulfan, carboplatin, carboquone, carmustine (BCNU), chlorambucil, chlornaphazine, cholophosphamide, chlorozotocin, cisplatin, cyclosphosphamide, dacarbazine (DTIC), estramustine, fotemustine, ifosfamide, improsulfan, lipoplatin, lomustine (CCNU), mafosfamide, mannosulfan, mechlorethamine, mechlorethamine oxide hydrochloride, melphalan, meturedopa, mustine (mechlorethamine), mitobronitol, nimustine, novembichin, oxaliplatin, phenesterine, piposulfan, prednimustine, ranimustine, satraplatin, semustine, temozolomide, thiotepa, treosulfan, triaziquone, triethylenemelamine, triethylenephosphoramide (TEPA), triethylenethiophosphaoramide (thiotepa), trimethylolomelamine, trofosfamide, uracil mustard and uredopa.

Suitable anti-metabolites may include, but are not limited to, aminopterin, ancitabine, azacitidine, 8-azaguanine, 6-azauridine, capecitabine, carmofur (1-hexylcarbomoyl-5-fluorouracil), cladribine, clofarabine, cytarabine (cytosine arabinoside (Ara-C)), decitabine, denopterin, dideoxyuridine, doxifluridine, enocitabine, floxuridine, fludarabine, 5-fluorouracil, gemcitabine, hydroxyurea (hydroxycarbamide), leucovorin (folinic acid), 6-mercaptopurine, methotrexate, nafoxidine, nelarabine, oblimersen, pemetrexed, pteropterin, raltitrexed, tegofur, tiazofurin, thiamiprine, tioguanine (thioguanine), and trimetrexate.

Non-limiting examples of suitable anti-tumor antibiotics may include aclacinomysin, aclarubicin, actinomycins, adriamycin, aurostatin (for example, monomethyl auristatin E), authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, epoxomicin, esorubicin, idarubicin, marcellomycin, mitomycins, mithramycin, mycophenolic acid, nogalamycin, olivomycins, peplomycin, plicamycin, potfiromycin, puromycin, quelamycin, rodorubicin, sparsomycin, streptonigrin, streptozocin, tubercidin, valrubicin, ubenimex, zinostatin, and zorubicin.

Non-limiting examples of suitable anti-cytoskeletal agents may include cabazitaxel, colchicines, demecolcine, docetaxel, epothilones, ixabepilone, macromycin, omacetaxine mepesuccinate, ortataxel, paclitaxel (for example, DHA-paclitaxel), taxane, tesetaxel, vinblastine, vincristine, vindesine, and vinorelbine.

Suitable topoisomerase inhibitors may include, but are not limited to, amsacrine, etoposide (VP-16), irinotecan, mitoxantrone, RFS 2000, teniposide, and topotecan.

Non-limiting examples of suitable anti-hormonal agents may include aminoglutethimide, antiestrogen, aromatase inhibiting 4(5)-imidazoles, bicalutamide, finasteride, flutamide, fluvestrant, goserelin, 4-hydroxytamoxifen, keoxifene, leuprolide, LY117018, mitotane, nilutamide, onapristone, raloxifene, tamoxifen, toremifene, and trilostane.

Examples of targeted therapeutic agents may include, without limit, monoclonal antibodies such as alemtuzumab, cartumaxomab, edrecolomab, epratuzumab, gemtuzumab, gemtuzumab ozogamicin, glembatumumab vedotin, ibritumomab tiuxetan, reditux, rituximab, tositumomab, and trastuzumab; protein kinase inhibitors such as bevacizumab, cetuximab, crizonib, dasatinib, erlotinib, gefitinib, imatinib, lapatinib, mubritinib, nilotinib, panitumumab, pazopanib, sorafenib, sunitinib, toceranib, and vandetanib.

Non-limiting examples of angiogenesis inhibitors may include angiostatin, bevacizumab, denileukin diftitox, endostatin, everolimus, genistein, interferon alpha, interleukin-2, interleukin-12, pazopanib, pegaptanib, ranibizumab, rapamycin (sirolimus), temsirolimus, and thalidomide.

Non-limiting examples of growth inhibitory polypeptides may include bortazomib, erythropoietin, interleukins (e.g., IL-1, IL-2, IL-3, IL-6), leukemia inhibitory factor, interferons, romidepsin, thrombopoietin, TNF-α, CD30 ligand, 4-1BB ligand, and Apo-1 ligand.

Non-limiting examples of photodynamic therapeutic agents may include aminolevulinic acid, methyl aminolevulinate, retinoids (alitretinon, tamibarotene, tretinoin), and temoporfin.

Other antineoplastic agents may include anagrelide, arsenic trioxide, asparaginase, bexarotene, bropirimine, celecoxib, chemically linked Fab, efaproxiral, etoglucid, ferruginol, lonidamide, masoprocol, miltefosine, mitoguazone, talapanel, trabectedin, and vorinostat.

Non-limiting examples of antibiotics may include penicillins, tetracyclines, cephalosporins, quinolones, lincomycins, macrolides, sulfonamides, glycopeptides, aminoglycosides, and carbapenems. Non-limiting examples of specific antibiotics may include amoxicillin, doxycycline, cephalexin, ciprofloxacin, clindamycin, metronidazole, azithromycin, sulfamethoxazole/trimethoprim, amoxicillin/clavulanate, and levofloxacin.

Non-limiting examples of anti-inflammatories may include diclofenac, etodolac, fenoprofen, flurbiprofen, ibuprofen, indomethacin, meclofenamate, mefenamic acid, meloxicam, nabumetone, naproxen, oxaprozin, piroxicam, sulindac, tolmetin, and celecoxib.

Also included are pharmaceutically acceptable salts, acids, or derivatives of any of the above listed agents. The dose of the chemotherapeutic agent can and will vary depending upon the agent and the type of tumor or neoplasm. A skilled practitioner will be able to determine the appropriate dose of the chemotherapeutic agent.

Other therapeutic agents may comprise a virus or a viral genome such as an oncolytic virus. An oncolytic virus comprises a naturally occurring virus that is capable of killing a cell in the target tissue (for example, by lysis) when it enters such a cell.

II. Computer-Implemented Methods and Systems

One aspect of the present disclosure encompasses a computer-implemented method for estimating subject-specific parameters of growth dynamics of a cancer tumor in a subject having a cancer tumor. The method comprises providing a computer system having at least one processor and associated memory comprising an approximate wave profile of a traveling wave solution obtained using a reaction-diffusion model of tumor growth. The approximate wave profile, the traveling wave solution, and the reaction-diffusion model of tumor growth can be as described in Section I.

The computer system comprises instructions to quantify morphological measures of the cancer tumor in the subject, the morphological features comprising a core, an invasive front, and tumor-associated tissue damage, and the measures comprising a volume of the core, a volume of the invasive front, and a volume of the tumor-associated tissue damage. The computer also comprises instructions to estimate the subject-specific parameters by fitting an approximate wave profile of a traveling wave solution to a tumor profile derived from the quantified measures from i, wherein the approximate wave profile is generated using a reaction-diffusion model of tumor growth.

The computer-implemented method further comprises inputting the morphological measures of the cancer tumor in the subject. The measures comprise measures of the inner core, the invasive front, and the maximum extent of tumor-associated tissue damage. Further, the computer-implemented method comprises processing the morphological measures to quantify the morphological measures and estimate the subject-specific parameters; processing the traveling solution profile of the mathematical cancer model to fit the solution profile to the idealized radii; and computing the subject-specific parameters of growth dynamics of the cancer tumor from the fitted traveling solution profile.

In some aspects, the computer-implemented method further comprises inputting descriptive information relating to the subject, the descriptive information comprising one or more data elements. The descriptive information can and will vary depending on the cancer tumor, the stage at which the tumor is diagnosed, and the subject, including age, and weight, among other variables. The data elements can include the results of clinical tests normally performed during a regular visit by the subject to a physician, including weight, height, blood pressure, pulse, and results of blood tests such as cholesterol levels, comprehensive metabolic panel, and lipid panel, among others. The data elements can also include information and results of clinical tests obtained during diagnosis of cancer. For instance, if the cancer tumor is GBM, the data elements can include family history, medical history, results of neurological exams, and medical images. During a neurological exam, a doctor can check balance, reflexes, coordination, vision, hearing, sensation, and short-term memory. The doctor can also look for signs of any external swelling around the eyes, caused by pressure on the optic nerve.

Another aspect of the present disclosure encompasses at least one non-transitory computer readable medium. The medium is stores instructions which, when executed, cause the at least one processor to receive imaging data from an imaging device. The one or more images can be images of the tumor and/or tumor-associated tissue damage.

The imaging data comprises measures of morphological features of a cancer tumor in a subject, the morphological features comprising a core and an invasive front of the front of the tumor, and tumor-associated tissue damage thereof, and the measures comprising a volume of the core, a volume of the invasive front, and a volume of the tumor-associated tissue damage. The instructions further cause the at least one processor to quantify the measures by deriving idealized radii representing a radius of the core, a radius to the invasive front, and a radius to an outer edge of tumor-associated tissue damage, and to estimate the subject-specific parameters by fitting an approximate wave profile of a traveling wave solution to a tumor profile derived from the measures. The approximate wave profile is generated using a reaction-diffusion model of tumor growth.

The medium can further comprise instructions, which when executed by the at least one processor cause the at least one processor to display subject-specific parameters of tumor growth dynamics, wherein the growth dynamics comprise motility, birth, and death dynamics of the tumor. Further, the medium can also comprise instructions, which when executed by the at least one processor cause the at least one processor to generate a report of the subject-specific parameters of tumor growth dynamics.

Yet another aspect of the present disclosure encompasses a system for estimating subject-specific parameters of growth dynamics of a cancer tumor in a subject. The system comprises an imaging device for obtaining morphological measures of the cancer tumor in the subject, the measures comprising measures of the inner core, the invasive front, and the maximum extent of tumor-associated tissue damage.

The system further comprises a processor. The processor comprises a memory having instructions stored thereon, wherein the instructions, when executed by the processor, cause the processor to perform the methods disclosed herein. By way of the processor-executable instructions, the processor is configured for quantifying the measures by deriving idealized radii representing the radius of the inner core, the radius to the invasive front, and the radius to the outer edge of tumor-associated tissue damage. Further by way of the processor-executable instructions, the processor is also configured for obtaining an approximate wave profile of a traveling wave solution obtained using a reaction-diffusion model of tumor growth and estimating subject-specific parameters by fitting the approximate wave profile to a tumor profile derived from the quantified measures.

In one aspect, the system also comprises an interface unit to display an output wherein the output is used for at least one of determining a personalized treatment protocol for the subject, staging the given disease in a patient, measuring response to therapy, phenotyping for patient selection to participate in drug trials, measuring stability of an anatomical structure, or predicting rate of change of the given disease. The interface unit may be, for example a display device such as, but not limited to a CRT (cathode ray tube) or LCD (liquid crystal display) monitor. The display device can display information to the user and may include or be in operative communication with an input device such as a keyboard, touchscreen, and/or pointing device (e.g., a mouse or a trackball). An input device may alternatively or in addition, be configured to receive and transmit a signal based on other types of user input, such as voice instruction, or body movement.

In some aspects, the processor is further configured by way of processor-executable instructions to obtain descriptive information relating to the subject, the descriptive information comprising one or more data elements. The descriptive information can be as described above.

An aspect of the disclosed system is shown in FIG. 7. In the aspect, an MRI machine 100 is used to image a GBM tumor using T1- and T2-weighted gadolinium contrast-enhanced MRI 110. The volumes of the inner necrotic core, the contrast-enhancing rim, and the outer edge of tumor-associated edema are obtained 210. A processor 200 quantifies the measures by deriving idealized radii representing the radius of the inner core (necrotic radius; $R_0$), the radius to the invasive front (enhancing radius; $R_1$), and the radius to the outer edge of tumor-associated tissue damage (T2 or maximum radius; $R_2$) 220. The processor 200 also obtains an approximate wave profile of a traveling wave solution obtained using a reaction-diffusion model of tumor growth 230, and estimates the parameters specific to the tumor by fitting the approximate wave profile of the model to a profile of the tumor derived from the idealized radii 240. The interface unit 300 displays the output of the subject-specific parameters of growth dynamics, wherein the growth dynamics comprise motility, birth, and death dynamics of the tumor 310. The output is used for determining a personalized treatment protocol for the subject, staging the tumor in the subject, measuring response of the tumor to therapy, phenotyping the tumor for subject selection to participate in drug trials, measuring stability of the tumor, or predicting rate of change of the tumor.

It should be understood that the disclosed methods, method steps and/or processor-executable instructions can be implemented or executed by means of any digital electronic system, computer hardware, firmware, software, or any combinations thereof. A processor may take the form of a programmable processor, a computer, or multiple computers, which may be programmed to perform the disclosed methods using any programming language. A program of instructions may comprise a stand-alone program or may have two or more modules, components, subroutines, or the like as known in the art of computer programming. Method steps can be performed by one or more programmable processors executing a computer program to perform functions or aspects of the methods, by operating on input data and generating output information.

A processor may be configured, by way of processor-executable instructions, to receive instructions and data from a memory device, which can be configured for storing instructions and data. A processor, or a computer containing a processor, may be in operative communication with at least one or more mass storage devices for storing data (e.g., magnetic, magneto-optical disks, or optical disks), such that the processor can receive data from or transfer data to such storage device(s). For example, data and/or instruction communications can be performed over a digital communications network.

It should be further understood that the disclosed methods, method steps and/or processor-executable instructions can be performed by a distributed computing system. A distributed computing system includes, for example, a front-end (user-end) interface, middleware, and a back-end, or any combination of two or more of these elements. A front-end component can be, for example, a client computer configured by way of processor-executable instructions to display a graphical user interface through which a user can interact with and provide input to the system. An interface can be embodied in a Web browser interface. A middleware component can be, for example, an application server. A back-end component can be, for example, a data server. Any or all of the components of such a distributed system can be in operative communication by way of one or more digital communications networks, which may be wired and/or wireless networks.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred aspects(s) thereof, the articles "a", "an", "the" and "said" are intended to mean that there are one or more of the elements. The terms "comprising", "including" and "having" are intended to be inclusive and mean that there may be additional elements other than the listed elements.

Methods according to the above can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, rackmount devices, standalone devices, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

As used herein, the term "treating" refers to (i) completely or partially inhibiting a disease, disorder or condition, for example, arresting its development; (ii) completely or partially relieving a disease, disorder or condition, for example, causing regression of the disease, disorder and/or condition; or (iii) completely or partially preventing a disease, disorder or condition from occurring in a patient that may be predisposed to the disease, disorder and/or condition, but has not yet been diagnosed as having it. Similarly, "treatment" refers to both therapeutic treatment and prophylactic or preventative measures. In the context of treating a cancer tumor, "treat" and "treating" encompass delaying or stopping the progression, or inducing remission of a cancer tumor, or reducing the severity of one or more symptoms associated with a cancer tumor.

As used herein, "therapeutically effective amount" or "pharmaceutically active dose" refers to an amount of a composition which is effective in treating the named disease, disorder or condition.

As various changes could be made in the above-described methods without departing from the scope of the invention, it is intended that all matter contained in the above description and in the examples given below, shall be interpreted as illustrative and not in a limiting sense.

EXAMPLES

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

The publications discussed throughout are provided solely for their disclosure before the filing date of the present application. Nothing herein is to be construed as an admission that the invention is not entitled to antedate such disclosure by virtue of prior invention.

The following examples are included to demonstrate the disclosure. It should be appreciated by those of skill in the art that the techniques disclosed in the following examples represent techniques discovered by the inventors to function well in the practice of the disclosure. Those of skill in the art should, however, in light of the present disclosure, appreciate that many changes could be made in the disclosure and still obtain a like or similar result without departing from the spirit and scope of the disclosure, therefore all matter set forth is to be interpreted as illustrative and not in a limiting sense.

Example 1. Introduction to Examples 2-5

Glioblastoma multiforme (GBM) is a highly aggressive primary brain cancer, with median survival time from diagnosis on the order of 15 months; long-term survival is extremely rare. Such rapid progression is promoted by highly proliferative and diffusely invasive cancer cells, which makes complete surgical removal impossible. Magnetic resonance imaging (MRI) is conventionally used to identify the location and characteristics of the tumor preoperatively, to guide surgery, and to monitor and track progression and treatment response. Perioperatively, MRI is used to guide the resection of the tumor mass, to assess post-operatively the volume of tumor resected, and to target other adjunct treatment such as radiation therapy.

GBMs morphologically typically appear (at least at initial diagnosis) as roughly spherical but highly heterogeneous masses that often exhibit a (crudely speaking) three-layer structure. Within the tumor there is usually extensive cell necrosis, often accompanied by tumor cells, and a cystic component as well. An outer region, which typically appears as contrast-enhancing on T1-weighted gadolinium contrast-enhanced MRI, is cytologically typified by proliferating cells that then infiltrate into surrounding brain tissue. The surrounding brain tissue is generally seen to be edematous on T2-weighted or T2-FLAIR MRI and at surgery, due to vasogenic edema. Prior statistical analyses have found that edema is a prognostic indicator of patient survival, but the relationship is complex and appears to be mediated by the expression of vascular endothelial growth factor and the activity of related angiogenic genes and various autocrine factors.

The standard of care for GBM patients was largely established by a clinical trial that comprises maximal surgical resection of the primary tumor, followed by six weeks of radiation to the gross tumor volume, plus a 2-3 cm margin, with concomitant oral temozolamide (TMZ), and 6-12 months of maintenance TMZ chemotherapy. Maximal surgical resection appears to offer some survival benefit. Nevertheless, the absolute survival benefit of even the most effective therapy is typically on the order of months. The highly infiltrative nature of GBMs makes recurrence nearly inevitable, even with maximal resection and aggressive adjuvant therapy, although individual tumors vary in their degree of invasiveness.

Given the grim situation, mathematical modeling has been proposed as a method to better understand the biophysical rules underlying GBM growth, with the ultimate goal to provide more effective therapy. Mathematical models have been widely applied to a variety of cancers and to cancer treatment in general, and GBM is the focus of many such works. A popular class of cancer models takes the form of a system of reaction-diffusion equations. In many cases, such systems generate a traveling wave solution, with the traveling wave speed of great interest, as it is an indicator of how fast the cancer progresses.

Variants of the Fisher-Kolmogorov equation, originally introduced in the 1930s, were first suggested as models for GBM growth. The Fisher-Kolmogorov model is given by:

$$\frac{\partial c}{\partial t} = \nabla \cdot (D \nabla c) + \rho c \left(1 - \frac{c}{K}\right), \quad (1.1)$$

where c(x, t) is the cancer cell density at location x and time t, D is a diffusion coefficient, ρ is the intrinsic tumor cell growth rate, and K is the local carrying capacity. (Variants include a linear version that replaces the logistic growth term with a simple exponential growth rate, pc.). It was reported that these parameters have been used to explore the effect of chemotherapy, to quantify patients' survival as a function of the extent of surgical resection, and to estimate the time of tumor initiation.

Net growth and diffusion parameters of model (1.1) may be estimated by image differencing when two sequential, pre-treatment patient MR series are available. Such a procedure is problematic, however, because changes in the tumor in images taken a few days or weeks apart tend to be small and are convolved with image co-registration errors. Some patients may be treated with steroids following initial diagnosis to reduce tumor-related edema and resulting neurological symptoms, which may alter the brain geometry and imaging appearance of the tumor at subsequent times.

Model (1.1) can yield a dense tumor core with an advancing front, but it cannot capture the heterogeneity between live and necrotic tumor cells, as it assumes that all cells are equally viable. While several modeling efforts have taken into account various proliferating, migrating, and necrotic cell components, they are too complicated to be reliably parameterized by the limited number of patient MRI series in typical clinical cases. Therefore, model (1.1) must be extended to include necrotic cells in a simplified way, such that patient-specific model parameters can be estimated from suitable measurements of MR images acquired at a single time point.

Example 2. Model Description

T1-weighted MRI sequences of GBM often show a partially necrotic core surrounded by a bright enhancing rim that correlates with high blood vessel density and, presumably, with rapid cell proliferation. Neurosurgical and biopsy studies indicate that this core and rim are usually surrounded by a large expanse of edema, which is best visualized on T2-weighted MRI and has been found to correspond with a component of diffusely invasive GBM cells. By approximating the tumor as a sphere, it may be possible to identify three idealized digital marks from imaging: necrotic radius, enhancing radius, and what we shall call the "T2" or "maximum" radius. It is hypothesized that a relatively simple mathematical model framework can capture all three of these digital marks and yield insights into the relative contributions of cellular proliferation, motility, and necrosis to the observed image features.

In these examples, it is demonstrated that the model has a traveling wave solution and the approximate wave profile is presented. A simple procedure to estimate patient-specific parameters by fitting the approximate wave profile to a tumor profile derived from patient MRIs is described. The identifiability of the model parameters is also discussed. This parameter estimation procedure is applied to obtain the key model parameters (consisting of the rate of cancer cell proliferation, death, and diffusion) for several patients.

The herein-proposed model of the growth of GBM is a system of reaction-diffusion equations:

$$\frac{\partial p}{\partial t} = \nabla \cdot \left[\left(\frac{Dp}{p+q}\right)\nabla(p+q)\right] + \tilde{g}(w)p - \tilde{\delta}(w)p, \quad (2.1a)$$

$$\frac{\partial q}{\partial t} = \nabla \cdot \left[\left(\frac{Dq}{p+q}\right)\nabla(p+q)\right] + \tilde{\delta}(w)p, \text{ where} \quad (2.1b)$$

$$w = 1 - p - q, \quad (2.2)$$

and p(x, t) and q(x, t) represent the proliferating and quiescent cell densities at time t and location x, respectively; quiescent cells are functionally equivalent to necrotic cells in this framework. It is assumed that the flux of total population due to migration is $-D\nabla(p+q)$, where D is a constant diffusion coefficient. It is further assumed that the proportion of the total flux contributed by each cell type equals its proportion of the total population. This form of diffusion was used to account for the key property of contact inhibition in cancer cell movement, with the underlying assumption that the two cell populations move together with equal motility, unaffected by necrotic cells. This type of model has successfully captured the structure of a growing tumor.

The per capita birth rate is $\hat{g}(w)$; proliferating cells become quiescent at the per capita rate δ(w), where w (Eq. 2.2)) represents the availability of space or some generic nutrient, which is called "growth factor" henceforth. The maximum cell density was scaled to be 1. In the model proposed herein, necrosis is not explicitly included but can be regarded as being lumped into q. Insofar as quiescent cells cannot become proliferative, δ(w) can be viewed as a functional death rate. The motivation in keeping the model framework relatively simple is to be able to estimate model parameters directly from clinical MRI imaging that is sparse in time.

To make the model biologically reasonable, the following constraints on g(w) and δ(w) were imposed:

$\tilde{g}'^{(w)} \geq 0$, $\tilde{\delta}(w) \leq 0$, $\tilde{g}(1) \geq \tilde{\delta}(1) = 0$, $\tilde{\delta}(0) > \tilde{g}(0) = 0$ That is, birth (death) should increase (decrease) with the availability of the growth factor, there is more birth than death at maximum values of the growth factor, and there is only death with no growth in the absence of the growth factor. It is also assumed that the death rate is negligible at maximum values of the growth factor. With these assumptions, it is numerically observed that with suitable initial conditions, the solution of (2.1) stays positive and is bounded (p+q≥1) for all t.

Only up to three parameters can be estimated based on the necrotic, enhancing, and maximum radii to be measured from MRI images. Therefore, a few more restrictions were placed on $\tilde{g}(w)$ and $\tilde{\delta}(w)$ to simplify the estimation of model parameters and to ensure their identifiability. It was assumed that the proliferation rate at maximum growth factor is ρ and that the death rate at zero growth factor is k and incorporate these parameters into $\tilde{g}$ and $\tilde{\delta}$, respectively; that is, $\tilde{g}(w=1; \rho) = \rho$ and $\tilde{\delta}(w=0; k) = k$. For reasons that will become clear later, a functional form that can be written as $\tilde{g}(w; \rho) = \rho g(w)$ and $\tilde{\delta}(w; k) = k\delta(w)$ was picked. Some examples include the cumulative distribution function of the beta distribution family (cf. the left pane of FIG. 4A-B). These additional assumptions impose little impact on the generality of our model. The benefit of including them is explained further below.

Example 3. Approximate Wave Profile

In most biological applications of reaction-diffusion models, solutions take the form of traveling waves. MRI images of GBM cancer growth suggest that we can approximate the evolution of the tumor by a traveling-wave solution of its growth model. To uniquely identify and accurately approximate GBM growth model parameters, it is highly desirable to obtain some analytic approximation of the traveling wave, to enable computational matching of the image wave profile and the approximate model wave profile. For this purpose, one spatial dimension is considered, which suffices insofar as the tumor is approximately spherical, and, at the time of diagnosis, its radius is large enough so that radial effects are negligible. With these assumptions, model (2.1) takes the form $$\frac{\partial p}{\partial t} = \frac{\partial}{\partial x}\left[\left(\frac{Dp}{p+q}\right)\frac{\partial}{\partial x}(p+q)\right] + \rho g(w)p - k\delta(w)p \quad (2.4a)$$

$$\frac{\partial q}{\partial t} = \frac{\partial}{\partial x}\left[\left(\frac{Dq}{p+q}\right)\frac{\partial}{\partial x}(p+q)\right] + k\delta(w)p. \quad (2.4b)$$

The system was nondimensionalised using the characteristic length $\sqrt{D/k}$ and the characteristic time $1/k$ so that $x = \sqrt{D/k}\hat{x}$ and $t = \hat{t}/k$, which leads to $$\frac{\partial p}{\partial \hat{t}} = \frac{\partial}{\partial \hat{x}}\left[\left(\frac{p}{p+q}\right)\frac{\partial}{\partial \hat{x}}(p+q)\right] + \hat{\rho}g(w)p - \delta(w)p \quad (2.5a)$$

$$\frac{\partial q}{\partial \hat{t}} = \frac{\partial}{\partial \hat{x}}\left[\left(\frac{q}{p+q}\right)\frac{\partial}{\partial \hat{x}}(p+q)\right] + \delta(w)p. \quad (2.5b)$$

where $\hat{\rho} = \rho/k$. A traveling wave solution of the form $p(\varepsilon_t) = p(\hat{x} - c\hat{t})$, $q(\varepsilon_t) = q(\hat{x} - c\hat{t})$ was sought, where c is the wave speed. Substituting these into (2.5) gives $$\frac{d}{d\xi}\left[\left(\frac{p}{p+q}\right)\frac{d}{d\xi}(p+q)\right] + c\frac{dp}{d\xi} + \hat{\rho}g(w)p - \delta(w)p = 0 \quad (2.6a)$$

$$\frac{d}{d\xi}\left[\left(\frac{q}{p+q}\right)\frac{d}{d\xi}(p+q)\right] + c\frac{dq}{d\xi} + \delta(w)p = 0. \quad (2.6b)$$

Linearizing at the wave head, i.e., substituting the ansatz $p = Ae^{-r\varepsilon_t}$ and $q = Be^{r-r\varepsilon_t}$ into (2.6), gives $(r^2 - cr + \hat{\rho})A = 0$. For a biologically realistic wave front, it is expected that A>0, B>0, and r>0. This requires that $c^2 > 4\hat{\rho}$, which implies that the minimum speed of the wave is $c_{min} = 2\sqrt{\hat{\rho}}$. It is numerically verified that the minimum speed is exactly the asymptotic speed, i.e., $c = c_{min}$.

To obtain an approximate wave profile, the wave coordinate was rescaled as $z = \varepsilon_t/c$, which leads to $$\frac{1}{c^2}\frac{d}{dz}\left[\left(\frac{p}{p+q}\right)\frac{d}{dz}(p+q)\right] - \frac{dp}{dz} + \hat{\rho}g(w) - p - \delta(w)p = 0, \quad (2.7a)$$

$$\frac{1}{c^2}\frac{d}{dz}\left[\left(\frac{q}{p+q}\right)\frac{d}{dz}(p+q)\right] - \frac{dq}{dz} + \delta(w)p = 0. \quad (2.7b)$$

Assuming that $1/c^2$ is small, each first term of (2.7) was neglected. Writing the resulting system in terms of p and w, the reduced system $$\frac{dp}{dz} = p(\hat{\rho}g(w) - \delta(w)), \quad (2.8a)$$

$$\frac{dw}{dz} = -\hat{\rho}pg(w), \quad (2.8b)$$

was obtained, which is amenable to phase plane analysis. The approximate wave solution corresponds to a trajectory that leaves (0, 1) and ends at (0, w*), with w*∈[0, 1) (see FIG. 1). (In Example 2, it was shown that such a trajectory exists, given the assumptions (2.3).) Dividing (2.8a) by (2.8b) yields $$\frac{dp}{dw} = \frac{\delta(w)}{\hat{\rho}g(w)} - 1. \quad (2.9)$$

Upon integration, p was obtained as a function of w, which will be used in the next section.

Figure 2:
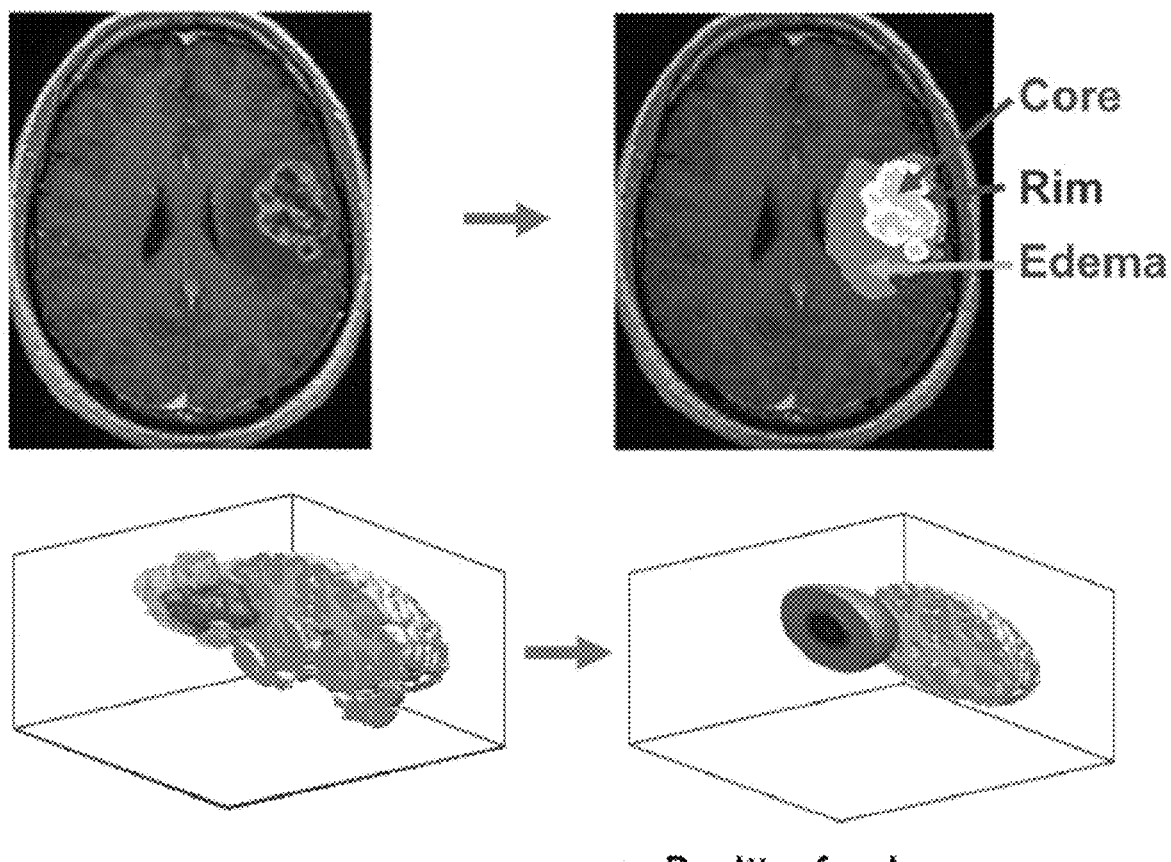
FIG. 2. The top half of the figure shows an example patient MRI registered to the standard brain domain, with the three tumor segments, necrotic core, enhancing rim, and tumor-associated edema highlighted on a single 2-D slice. The full 3-D segmentation, and the equivalent tumor sphere with associated radii, $R_0$, $R_1$, and $R_2$, is shown in the lower half.

From clinical MRI data, three idealized radii: $R_0$, $R_1$, and $R_2$ are derived, representing respectively the radius of the inner necrotic core, the radius to the edge of the contrast-enhancing rim, and the radius to the outer edge of tumor-associated edema. Such data have been extracted from a series of anonymized patient MRI data consisting of T1-contrast enhanced and T2-weighted MRIs at initial diagnosis. Using the publicly available MATLAB software package, Statistical Parametric Mapping 12 (SPM 12), MRIs are initially registered to a standard brain space, and then, using Slicer 3D software, the total necrotic core volumes, enhancing rim volumes, and tumor-associated edema volumes are determined from semi-manual tumor segmentation. Finally, these volumes are converted to radii assuming a spherical tumor geometry. The width of the proliferating rim, denoted as $L_1$, and the width of the edematous rim, denoted as $L_2$, can be calculated as $L_1=R_1-R_0$ and $L_2=R_2-R_1$, as demonstrated visually in FIG. 2 and FIGS. 3A-B.

Contrast-enhancing regions of T1-weighted images are assumed to correspond to high densities of proliferating tumor cells, and edematous regions on T2-weighted imaging are assumed to correspond to low densities. The respective detection thresholds for T1 and T2 imaging are denoted as $a_1 p_{max}$ and $a_2 p_{max}$, where $0<a_2<a_1<1$ and $p_{max}=\max_z p(z)$, i.e., the maximum density of proliferating cells given by the traveling wave solution.

Example 3a. Approximate Wave Profile for which Sequential MRI Series are Available Often only a single MRI series is available before surgery (see Example 2b below), although in some cases, a diagnostic MRI followed some days or weeks later by a pre-surgery MRI may be available. In the latter case, the image-derived wave velocity V is the change in tumor radius divided by the length of the time interval.

Figure 3B:
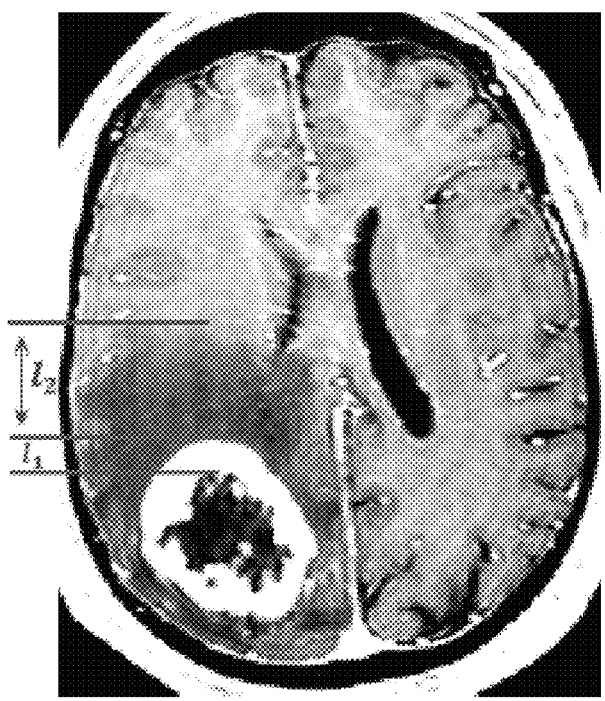
FIG. 3B. Tumor profile seen in MR image. Parameter estimation is done by matching model-derived quantities, e.g., l1 and l2, to the corresponding image-derived ones.

From the approximate wave profile, the corresponding quantities are computed to match with MR images (cf. FIGS. 3A-B). The rim width (in dimensional form) is computed as:

$$\ell_1 = \frac{2\sqrt{D\rho}}{k} \int_{w_1^-}^{w_1^+} \frac{dz}{dw} dw, \qquad (2.10a)$$

$$\ell_2 = \frac{2\sqrt{D\rho}}{k} \int_{w_2}^{w_1^-} \frac{dz}{dw} dw, \qquad (2.10b)$$

where $w_1^{+/-}$ and $w_2$ satisfy, respectively, $p(w_1^{+/-})=a_1 p_{max}$ and $p(w_2)=a_2 p_{max}$. Here $p(w)$ is obtained by integrating Eq. (2.9) (see appendix for details). Additionally, the model-derived wave speed $c=2\sqrt{\rho D}$ can be matched with image-derived speed V. Thus, three nonlinear equations are obtained $$l_1=L_1,\ l_2=L_2,\ c=V$$

from which the parameters D, $\rho$, and k are found. Given the assumptions, the ratio of (2.10a) and (2.10b) can be taken, which gives $$f(\hat{\rho}) \equiv \frac{\int_{w_1^-}^{w_1^+} \frac{dz}{dw} dw}{\int_{w_2}^{w_1^-} \frac{dz}{dw} dw} = \frac{L_1}{L_2}, \qquad (2.12)$$

insofar as the integrals are functions of $\hat{\rho}$. Equation (2.12) can be solved for $\hat{\rho}$ analytically in special cases or numerically in general. The monotonicity of $f(\cdot)$ is important for the identifiability of parameters. Once $\hat{\rho}$ is found, i.e., the ratio $\rho/k$, all parameters can be found by back substitution.

Example 3b. Approximate Wave Profile for which a Single MRI Series is Available The above method requires two MR scans taken at two consecutive times prior to surgery to obtain an image-derived estimate of wave speed. If no second MR series is available, then tumor age may be estimated by the tumor radius divided by the wave speed. However, the estimate depends on which radius ($R_1$ or $R_2$) is used, because the tumor grows exponentially at first and linearly later on. This initial exponential growth stage needs to be taken into account as a correction to the aforementioned tumor age estimation. Suppose that for $0 \leq t \leq t^*$, quiescence is negligible and the proliferating cancer cells grow exponentially from a point source of density $p_0$, and that for $t>t^*$, the tumor grows as a traveling wave with speed $2/\sqrt{\rho D}$. By equating the two age estimates, the following is obtained:

$$\frac{R_1 - R_1^*}{2\sqrt{\rho D}} = \frac{R_2 - R_2^*}{2\sqrt{\rho D}}, \qquad (2.13)$$

$$R_i^* = t^* \sqrt{4D\rho - \frac{4D}{t^*} \ln\left(\frac{a_i(4\pi D t^*)^{3/2}}{p_0}\right)}, \ i = 1, 2, \qquad (2.14)$$

where $R_1$ and $R_2$ are respectively the T1 and T2 radii at $t=t^*$ (see details of $R_1^*$ and $R_2^*$ in the appendix).

Replacing the last equation in (2.11) with (2.13) provides three equations. To solve them for the unknown parameters, (2.10a) is taken over (2.10b) as before to obtain (2.12). It can then be solved for the ratio $\hat{\rho}=\rho/k$. Substituting this expression back to either $l_1=L_1$ or $l_2=L_2$ gives the ratio $\rho/D$. Finally, expressing D and k in terms of $\rho$, (2.13) can be solved for $\rho$, and D and k follow.

Example 4. Traveling Wave Solutions

In the following, the existence of traveling-wave solutions in system (2.8) is rigorously established, first showing that the solutions of system (2.8) with positive initial values are non-negative and bounded.

Lemma 1. Assume that $g(w)=wG(w)$, where $G(w)$ is a bounded function. Then the solutions of system (2.8) with positive initial values are positive and bounded.

Proof: If $x'=x\ f(t, x)$ and f is a bounded function, then $x(t)=x(t_0) \exp(\int_{t_0}^t f(s,x(s))ds)$, which is positive whenever $x(t_0)>0$. Since $$\frac{d(p+w)}{dz} = -\delta(w), \qquad (4.1)$$

Thus (p+w) is bounded, which implies that both p and w are also bounded.

For any $w^* \in [0, 1]$, the point $(0, w^*)$ is an equilibrium of (2.8).

Theorem 1. System (2.8) admits positive traveling-wave solutions that correspond to heteroclinic orbits connecting the steady state (0, 1) to another steady state, (0, w*).

Proof A detailed phase plane analysis of (2.8) is made to show the existence of a trajectory that starts from (1, 0) and ends at (w*, 0), where $w^* \in [0, 1)$. (See FIG. 1) Given:

$$\frac{dp}{dw} = \frac{\delta(w)}{\hat{\rho}g(w)} - 1, \qquad (4.2)$$

$$\frac{d^2 p}{dw^2} = \frac{\delta'(w)g(w) - \delta(w)g'(w)}{\hat{\rho}g(w)^2}, \qquad (4.3)$$

Since $g(w)$ and $\delta(w)$ are both positive functions and $g'(w)>0$ and $\delta'(w)<0$ on $w \in [0, 1]$, it follows that $d^2p/dw^2<0$ for all $w \in [0, 1]$.

It is first shown that the trajectory starting from (1, 0) will never cross the line p=1−w. Because g(1)=1, we have δ(1)=0, and therefore, $dp/dw|_{w=1}=-1$. Since $d^2p/dw^2<0$, the slope of a trajectory with w<1 will be greater than −1, which means it will not cross the line p=1−w. Also, because the solution components stay positive, the trajectory starting from (1, 0) will never cross the p-axis from right to left.

Because the functions g and δ are monotone, there is a unique value $w^t \in (0, 1)$ such that $dp/dw|_{w=w^t}=0$. Moreover, $dp/dw|_{1>w>w^t}>0$ while $dp/dw|_{0<w<w^t}<0$.

Insofar as w is strictly decreasing and bounded from below by 0, there exists some $w^* \in (0, 1)$ such that $\lim_{z\to\infty} w(z)=w^*$. It is claimed that $w^*<w^t$. Otherwise, p is a non-decreasing function, which implies that the trajectory approaches a positive steady state $E^*=(p^*, w^*)$. However, the system (2.8) does not admit any positive steady states.

Let $a \in (w^*, w^t)$ and $b=\hat{\rho} g(a)-\delta(a)<0$. Since $\lim_{z\to\infty} w(z)=w^*$, there is a $z^*>0$ such that for $z \geq z^*$ and w<a. Therefore, for $z \geq z^*$, $dp/dz<bp$, which implies that $\lim_{z\to\infty} p(z)=0$. Hence, system (2.8) admits positive traveling-wave solutions that correspond to heteroclinic orbits connecting the steady state (0, 1) to another steady state, (0, w*).

Rim width.

Figure 1:
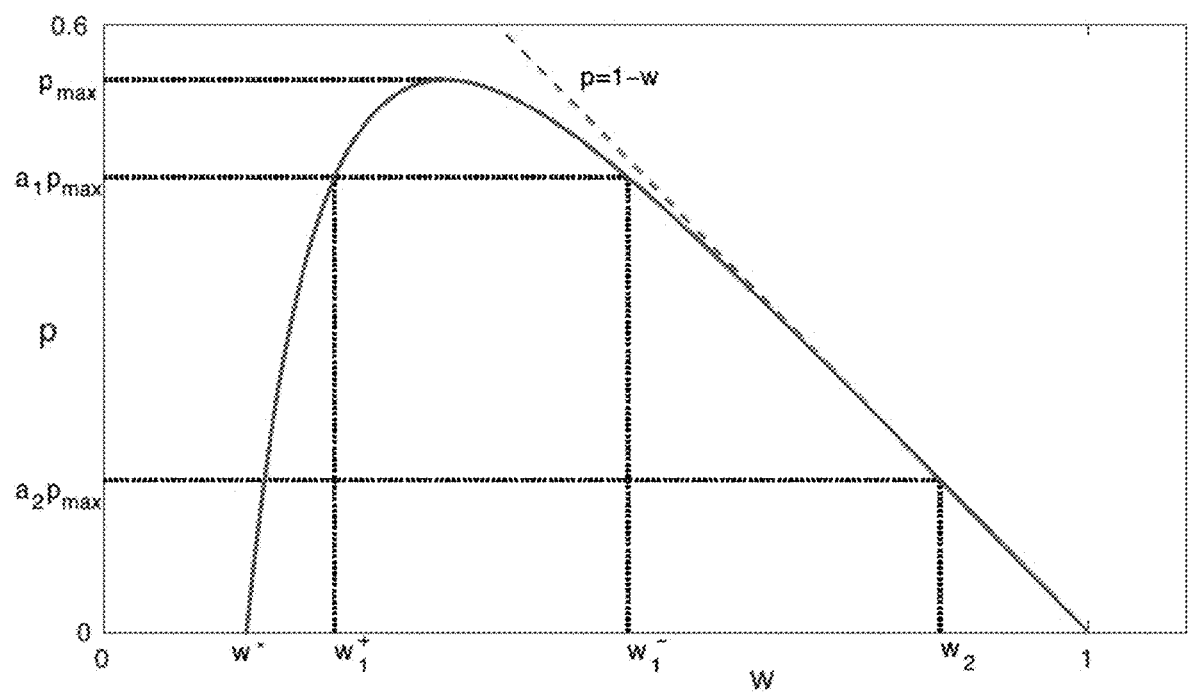
FIG. 1. A typical trajectory that connects (0, 1) and (0, w*) in the phase plane. Given $\delta(w)$ and $g(w)$, this trajectory can be found by integrating (2.9). It represents an approximate traveling wave solution. See Example 3 for a proof of its existence under general assumptions.

The trajectory in FIG. 1 corresponds to a traveling wave profile in the z coordinate as shown in FIG. 3A. Because of the choice of nondimensionalization, $x=-(2\sqrt{D\rho/k})z$, by definition the rim width in the dimensional form is $$\ell_1 = \frac{2\sqrt{D\rho}}{k}(z_1^+ - z_1^-) = \frac{2\sqrt{D\rho}}{k}\int_{z_1^-}^{z_1^+} dz \quad (4.4)$$

where $p(z^{+/-}_1)=a_1 p_{max}$. p was taken as a function of z (cf. FIG. 3A). w was also taken as a function of z to make a change of variable to the above integral, which gives Eq. (2.10a). A similar argument applies to (2.10b).

Derivation of $R^*_1$ and $R^*_2$

Figure 6:
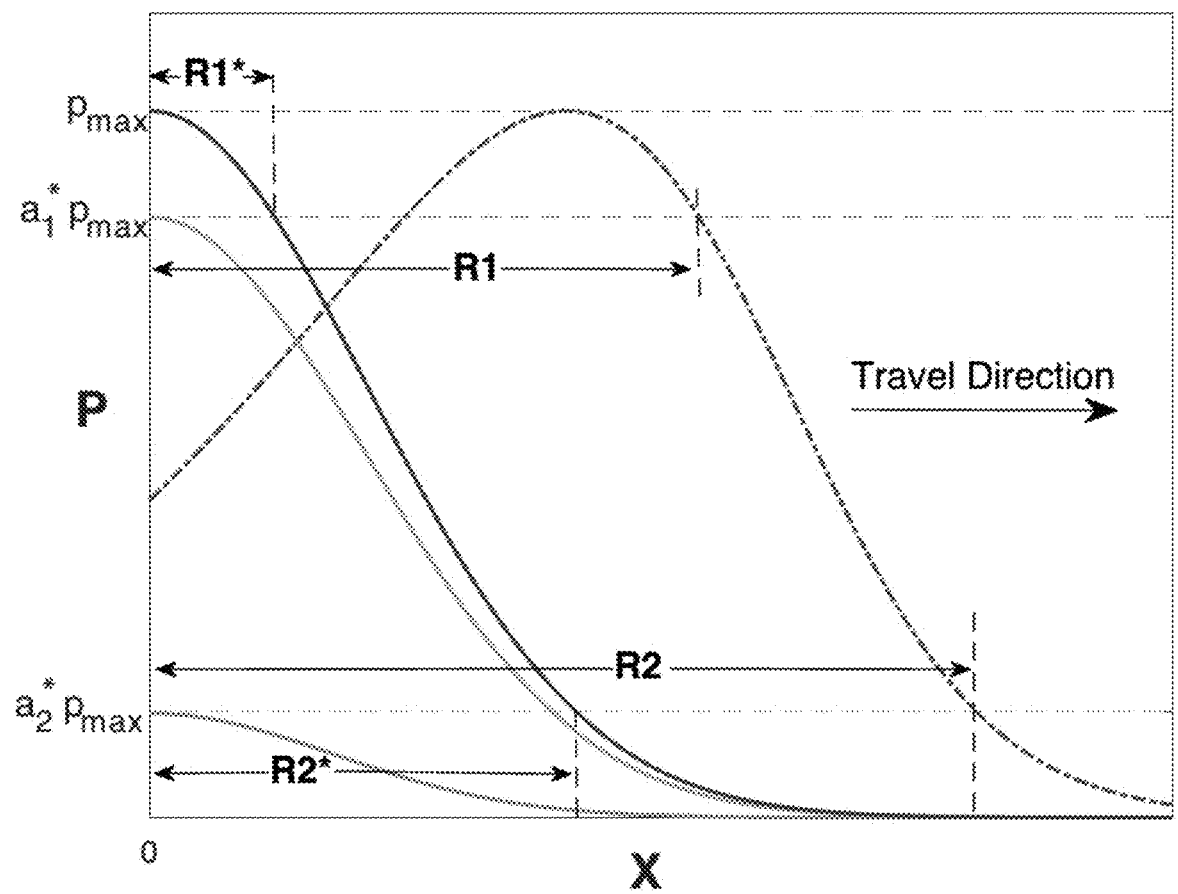
FIG. 6. The transition of wave profile based on the two-stage tumor growth model. The dotted (purple) curve represents a stable wave profile generated by system (2.8). The solid curves are generated by Eq. (4.5) and represent the tumor's exponential growth phase. The stable wave profile is formed after the exponential growth curve reaches $_{pmax}$ (red solid curve).

Tumor growth can be separated into two stages. First, the tumor cells grow exponentially until the cell density is high enough ($\rho_{max}$) to form a stable wave profile. Afterward, the growth of tumor cells is described by (2.8). The radii $R_1$ and $R_2$ are observed from clinical MRI data and correspond respectively to the distance from the center of the tumor to the edge of the enhancing rim and to the edge of the edematous region on T2 imaging; they correspond to tumor dynamics before the stable wave profile has formed (cf. FIG. 6).

During the exponential growth phase, say from 0<t<t*, quiescence is negligible and the governing equation of tumor cell density is $$\frac{\partial p}{\partial t} = D\frac{1}{r^2}\frac{\partial}{\partial r}\left(r^2 \frac{\partial p}{\partial r}\right) + \rho p, \quad (4.5)$$

where spherical symmetry is used, as it is assumed that the tumor is spherical when its radius is small. This linear equation has the Green's function $$p(r, t) = \frac{1}{(4\pi Dt)^{3/2}} \exp\left(\rho t - \frac{r^2}{4Dt}\right) \quad (4.6)$$

Suppose that the tumor starts at t=0 as a point source with density $p_0$. It follows that at t=t*, the position of the tumor front at density $p=a_i$ is given by Eq. (2.14).

Example 5. Using the Developed Model

Figure 4A:
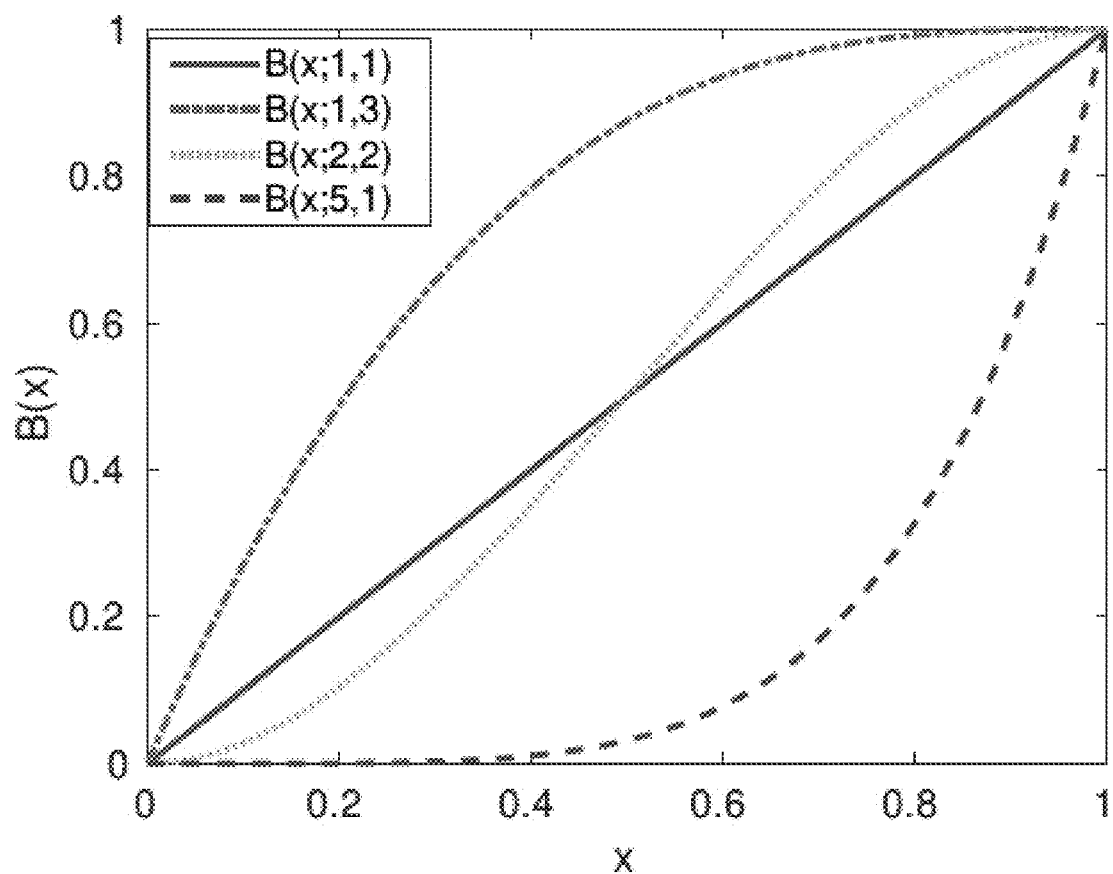
FIG. 4A. Cumulative distribution functions of some beta distributions. These functions satisfy Eq. (2.3) and serve as candidates to represent biological response to limitation of growth factors.
Figure 4B:
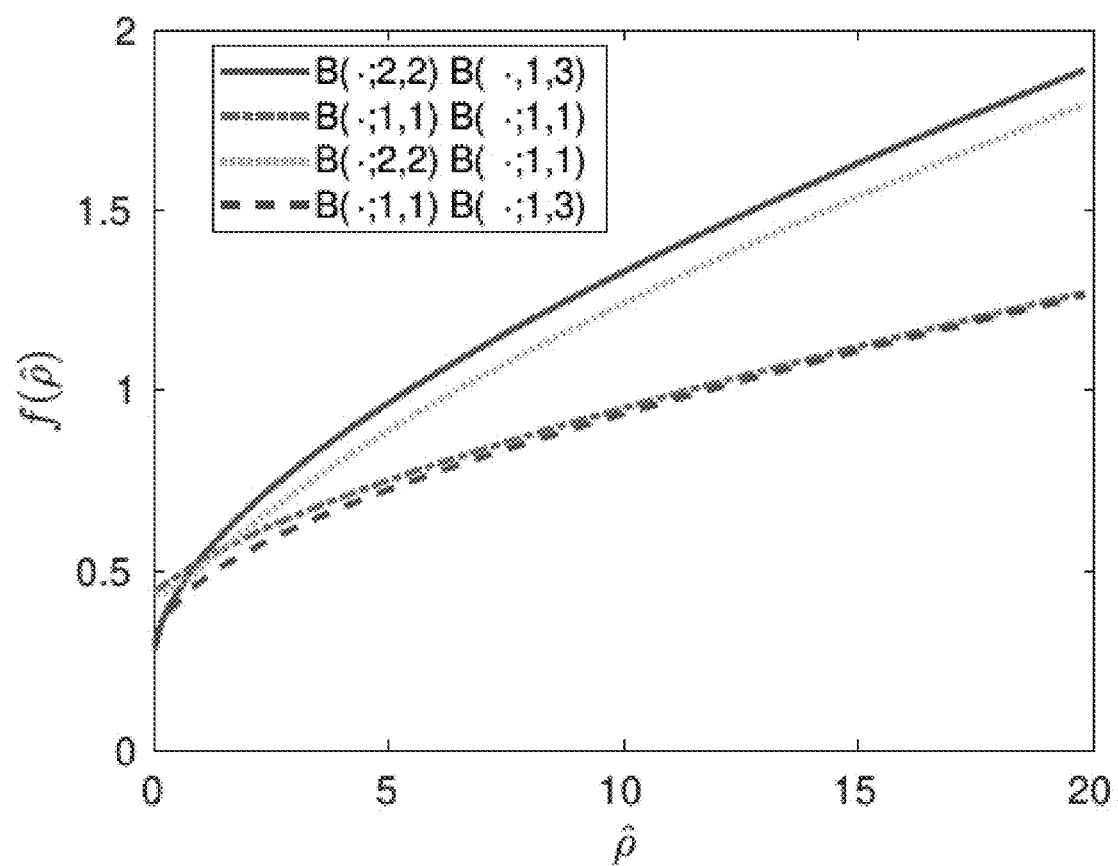
FIG. 4B. Monotonicity of $f(\hat{p})$ given different choices of $g(w)$ and $\delta(w)$ as indicated in the legend. All choices lead to a monotonic function $f(\cdot)$ and hence identifiable parameters.

Monotonicity is crucial for parameter identifiability, so the monotonicity of f(·) was first investigated for some specific choices of g(w) and δ(w). Given the restrictions described in Example 2, the cumulative density function (CDF) of the Beta distribution family suits our purposes. Therefore, let $g(w)=B(w; \alpha_\delta, \beta_\delta)$ and $\delta(w)=1-B(w; \alpha_\delta, \beta_\delta)$, where B(w; α, β) is the CDF of the beta distribution with shape parameters α and β. By varying α and β, generated linear, sigmoidal, and concave up/down curves (FIG. 4A). The framework is robust to those choices, that is, the monotonicity of f(ρˆ), defined by Eq. (2.12), is preserved (FIG. 4B). Sigmoidal-shaped growth and death functions (g and δ, respectively) may provide biologically realistic response functions to limited growth factors (most enzymatic reaction rates have sigmoidal shapes with respect to reactant concentration). Given this family of functions, the question of estimating patient-specific tumor growth and death rates from MR imaging was considered.

The model was parameterized with patient data in which there is only one MRI scan before surgery. Table 1 summarizes the image-derived tumor radii and the corresponding parameters estimated by the method introduced in the previous section. The parameters $a_1=0.9$ and $a_2=0.1$ are adapted from values found in the literature [33], while $p_0=0.02$ and t*=60 days are hypothetical values. The parameters vary considerably among individual patients.

Figure 5:
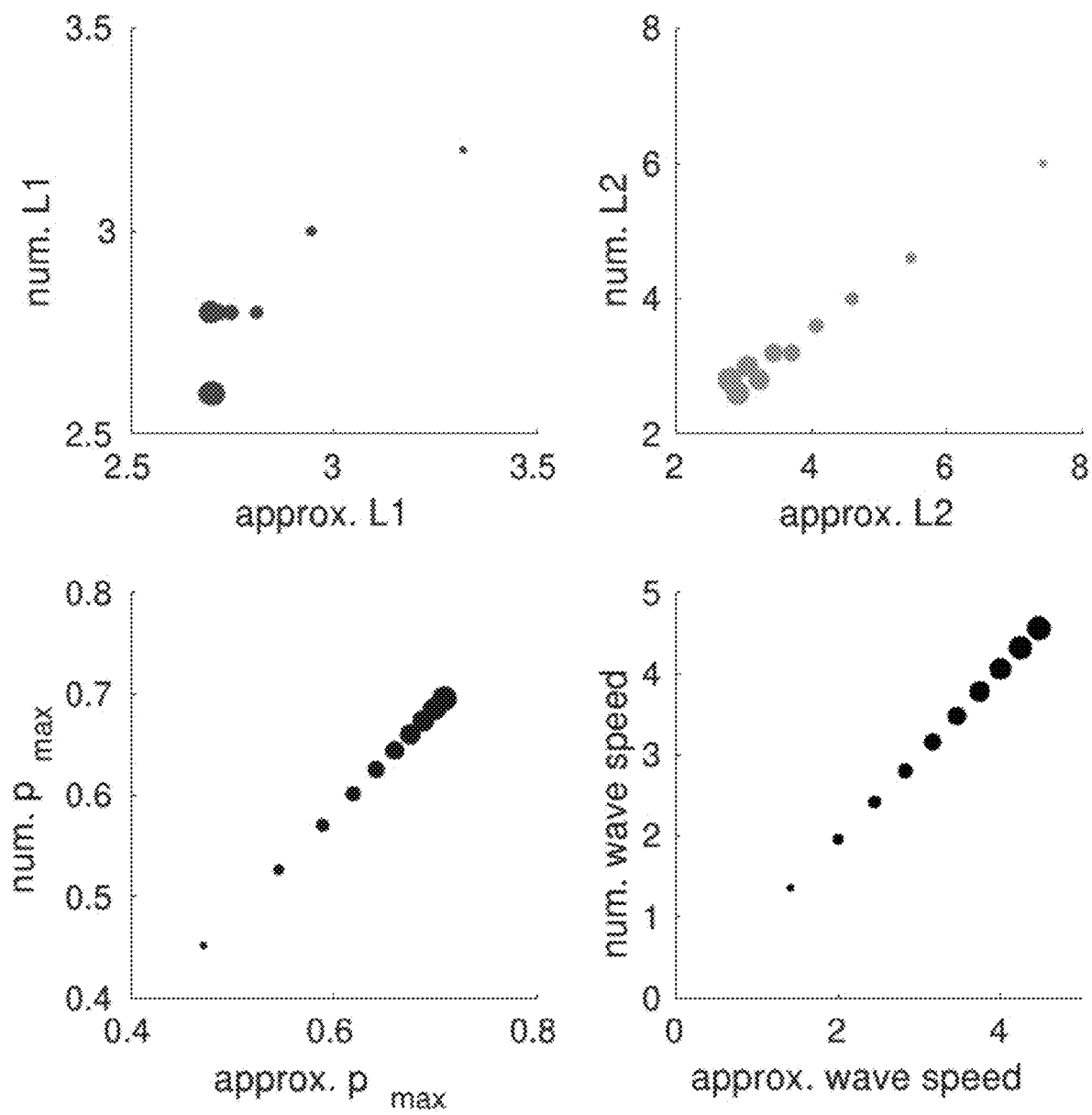
FIG. 5. Scatter plots of approximate wave profile characteristics (on horizontal axis) versus the ones obtained by numerical simulation (on vertical axis) for a range of r̂ from 0.5 to 5 by increments of 0.5. The size of the dot corresponds to the value of ρ̂. The dots scatter closely to the diagonal line with slope 1, indicating agreement between the numerical solution and our approximation.

The approximate quantities were compared to those obtained from the numerical solution of the model. As shown in FIG. 5, the approximated results match well with the numerical results except for some discrepancy for $L_2$ when ρˆ is small. This result is not a surprise, because the approximation assumes that $c=2\sqrt{\rho}$ˆ is large. Moreover, the numerical approximation of $L_2$ is prone to errors due to the fixed grid size and large rate of change around the threshold of $L_2$. Overall, it is believed that the approximation is accurate for the parameter ranges estimated from the image data.

TABLE 1

| Patient | $R_0$ (mm) | $R_1$ (mm) | $R_2$ (mm) | D (mm$^2$day$^{-1}$) | ρ (day$^{-1}$) | k (day$^{-1}$) |
|---|---|---|---|---|---|---|
| 1 | 14.87 | 20.73 | 27.77 | 0.2852 | 0.2102 | 0.0602 |
| 2 | 20.48 | 26.34 | 38.24 | 1.2791 | 0.2624 | 0.3537 |
| 3 | 6.61 | 10.91 | 15.24 | 0.0825 | 0.1736 | 0.0327 |
| 4 | 22.87 | 26.96 | 37.03 | 0.9825 | 0.2590 | 0.7819 |
| 5 | 8.17 | 14.20 | 25.10 | 0.9769 | 0.2520 | 0.2260 |
| 6 | 8.29 | 15.83 | 20.35 | 0.0687 | 0.1652 | 0.0106 |

Radii of equivalent tumor sphere derived from T1 and T2 images and the corresponding vital parameters estimated by our protocol. We have preset $a_1=0.9$, $a_2=0.1$, $p_0=0.02$ mm and t*=60 days.

Discussion for Examples 2-5

In this work, the Fisher-Kolmogorov reaction-diffusion model of GBM growth was extended, Eq. (1.1), to explicitly separate the cancer cell birth and death (or quiescence) processes, which are described in terms of generic functions that depend upon an implicit nutrient or growth factor. The birth and death processes, g(w) and δ(w), respectively, were specified by the cumulative distribution function of a beta distribution, each uniquely specified by a single parameter, ρ and k. Thus, along with the diffusion coefficient, D, the model describes cancer growth via three parameters, D, ρ, and k, and yields a tumor morphology (in one dimension) consisting of a necrotic core, a high-density rim, and an outer low density rim, which may correlate to three radii, $R_0$, $R_1$, and $R_2$, that can be estimated from a single patient MR image.

It was demonstrated that the reaction-diffusion system has a traveling-wave solution, which is common in such systems. Studies on this topic date back to the Fisher's work in the 1930s on the spread of advantageous genes. Rigorous proof of the existence of traveling wave solution in a reaction-diffusion system often leads to phase space analysis such as the one on diffusive Lotka-Volterra equations. Although in general a rigorous proof of a traveling-wave solution is a daunting task, the instant reduced system is amenable to phase plane analysis, and the orbit that represents the traveling wave solution can be identified (see Examples 4 and 5).

Via traveling wave analysis, a method to estimate D, ρ, and k was developed from as few as a single magnetic resonance image, based on certain growth assumptions. These parameters were estimated for six patient test cases, as shown in Table 1. Because of the sparsity of imaging data for a typical patient, parameter identifiability in this case is provided by the monotonicity of the function $f(\cdot)$ (as seen in left pane of FIG. 4A-B); the instant approach differs from more common statistical practices that are appropriate when more data are available.

Disaggregating the net cell proliferation into birth and death processes not only aids in relating (simplified) tumor appearance on MRI to the model parameters, but it may provide useful valuable information for personalized treatment design, insofar as chemotherapy and radiotherapy target proliferating cells. Moreover, the structural information is also potentially useful, as drug dosages might be selected to ensure penetration through the width of the proliferating rim. Research along this general line has been conducted using model (1.1).

The instant analysis uses a more complex description of motility than simple diffusion. The diffusion term in Eq. (2.4) belongs to a more general category called cross diffusion. It represents the phenomenon in which the gradient in the concentration of one species causes a flux of another species. The type of cross diffusion considered in the Examples herein has been studied in a more general and theoretical context. In a modeling study of a vascular tumour growth, the adoption of a proportion-based cross diffusion in a tumor-growth model was justified by recognizing that tumor cell migration is "contact inhibited": the presence of one type of cell halts the movement of the other. This type of cross diffusion can cause the solution to become negative, but we have not encountered this difficulty so far in our numerical simulations.

Despite the existence of many possible diffusion terms, the exact form of diffusion does not matter in the one-dimensional analysis, because the second derivatives are dropped in model (2.7). However, the diffusion coefficient does play an important role in the linearized wave head, where it affects the wave speed, and in the characteristic length where its square root scales the space. The scale-invariant part of the wave profile is mostly determined by the exact forms of the birth and death functions.

Presented herein are two novel methods to make patient-specific estimates of a three-parameter model of GBM growth from the limited MRI data that is typically available in clinical settings. It is possible to estimate the model parameters from a single pre-surgery image. Improved estimates are possible when images are acquired at multiple time points.

What is claimed is:

1. A method of estimating subject-specific parameters of growth dynamics of a cancer tumor in a subject comprising:
   a. imaging the subject with a magnetic resonance image (MRI) machine to obtain clinical imaging data comprising MR images associated with the cancer tumor in the subject;
   b. obtaining measures of morphological features of the cancer tumor in the subject from the clinical imaging data, the morphological features comprising an inner core, an invasive front, and tumor-associated tissue damage, and the measures comprising a volume of the core, a volume of the invasive front, and a volume of the tumor-associated tissue damage;
   c. quantifying the measures by deriving idealized radii representing a first radius of the core, a second radius to the invasive front, and a third radius to an outer edge of tumor-associated tissue damage;
   d. obtaining an approximate wave profile of a traveling wave solution generated using a reaction-diffusion model of tumor growth that incorporates a growth factor defined in terms of a proliferating cell density and a quiescent cell density of the cancer tumor, the traveling wave solution being defined in terms of the proliferating cell density and the quiescent cell density of the cancer tumor; and
   e. estimating subject-specific parameters by fitting the approximate wave profile to a tumor profile derived from the quantified measures from (c);
   wherein the growth dynamics comprise motility, birth, and death dynamics of the cancer tumor.

2. The method of claim 1, wherein the idealized radii are quantified by approximating the cancer tumor and the morphological features of the cancer tumor as a sphere, and identifying radii including the first radius of a sphere representing the inner core, the second radius of a sphere representing the invasive front, and the third radius of a sphere representing the outer edge of tumor-associated tissue damage.

3. The method of claim 1, wherein the MR images are T1-weighted and T2-weighted MR images of the cancer tumor.

4. The method of claim 1, wherein clinical imaging data comprise a single MR image or an MRI sequence taken at a single time point.

5. The method of claim 1, wherein clinical imaging data comprise a single MR image or an MRI sequence taken at a single time point prior to surgery.

6. The method of claim 1, wherein the clinical imaging data comprise images acquired at two consecutive time points prior to surgery.

7. The method of claim 1, wherein the method further comprises using the estimated parameters of growth dynamics of the cancer tumor to estimate time of initiation of the cancer tumor.

8. The method of claim 1, wherein estimating subject-specific parameters includes:
   determining a value of a nondimensionalized intrinsic tumor cell growth rate $\hat{\rho}$;

back-substituting the nondimensionalized intrinsic tumor cell growth rate $\hat{\rho}$ into the tumor profile to obtain a ratio $\rho/D$, where $\rho$ is an intrinsic tumor cell growth rate of the subject-specific parameters and D is a diffusion coefficient of the subject-specific parameters;

determining the intrinsic tumor cell growth rate $\rho$ based on the ratio $\rho/D$;

determining the diffusion coefficient D based on the ratio $\rho/D$; and determining a death rate k when the growth factor w is equal to zero based on the ratio $\rho/D$ and the nondimensionalized intrinsic tumor cell growth rate $\hat{\rho}$.

9. The method of claim 1, wherein the reaction-diffusion model of tumor growth is a three-parameter reaction-diffusion model of tumor growth derived from the Fisher-Kolmogorov equation.

10. The method of claim 9, wherein the reaction-diffusion model of tumor growth is system of reaction diffusion equations defined as:

$$dp/dz = p(\hat{\rho}g(w) - \delta(w)),$$

$$dw/dz = -\hat{\rho}pg(w),$$

where $\hat{\rho}$ is indicative of a nondimensionalized intrinsic tumor cell growth rate;

p is indicative of the proliferating cell density;

q is indicative of the quiescent cell density;

w is indicative of the growth factor defined in terms of the proliferating cell density and the quiescent cell density as $w = 1 - p - q$;

g(w) is indicative of birth rate defined in terms of the growth factor w;

$\delta(w)$ is indicative of a necrosis rate at which proliferating cells become necrotic and is defined in terms of the growth factor w; and z is indicative of a rescaled wave coordinate defined by as $z = -\varepsilon_t/c$, where $\varepsilon_t$ is obtained from the traveling wave solution in terms of the proliferating cell density p and the quiescent cell density q and where c is a wave speed.

11. The method of claim 10, wherein the model is used to obtain an approximate wave profile of the traveling wave solution that mimics tumor progression, with the speed of the traveling wave being an indicator of speed of tumor progression and where the traveling wave solution incorporates the proliferating cell density p and the quiescent cell density q throughout tissue such that $p(\varepsilon_t) = p(\hat{x} - c\hat{t})$ and $q(\varepsilon_t) = q(\hat{x} - c\hat{t})$, where $\hat{x}$ is a nondimensionalized location based on the location x and where $\hat{t}$ is a nondimensionalized time based on the time t.

12. The method of claim 10, wherein fitting the approximate wave profile to a tumor profile comprises:

determining a first width $L_1$ of a proliferating rim of the cancer tumor based on the first radius and the second radius;

determining a second width $L_2$ of an edematous rim of the cancer tumor based on the second radius and the third radius; and fitting the approximate wave profile to a tumor image wave profile derived from the first radius of the inner core, the second radius to the invasive front, and the third radius to the outer edge of tumor-associated tissue damage by relation of the nondimensionalized intrinsic tumor cell growth rate $\hat{\rho}$, the rescaled wave coordinate z, and the growth factor w with the first width $L_1$ of the proliferating rim of the cancer tumor and the second width $L_2$ of the edematous rim of the cancer tumor.

13. The method of claim 1, wherein the cancer tumor is glioblastoma multiforme (GBM).

14. The method of claim 13, wherein the inner core is inner necrotic core, the invasive front correlates with high blood vessel density, and the outer edge of tumor-associated tissue damage is the outer edge of tumor-associated edema.

15. At least one non-transitory computer readable medium storing instructions which when executed by at least one processor, cause the at least one processor to:

a. receive imaging data from an imaging device, wherein the imaging data comprises measures of morphological features of a cancer tumor in a subject, the morphological features comprising a core and an invasive front of the front of the cancer tumor, and tumor-associated tissue damage thereof, and the measures comprising a volume of the core, a volume of the invasive front, and a volume of the tumor-associated tissue damage;

b. quantify the measures by deriving idealized radii representing a first radius of the core, a second radius to the invasive front, and a third radius to an outer edge of tumor-associated tissue damage; and c. estimate subject-specific parameters by fitting an approximate wave profile of a traveling wave solution to a tumor profile derived from the measures from (a), wherein the approximate wave profile is generated using a reaction-diffusion model of tumor growth that incorporates a growth factor defined in terms of a proliferating cell density and a quiescent cell density of the cancer tumor, the traveling wave solution being defined in terms of the proliferating cell density and the quiescent cell density of the cancer tumor.

16. The at least one non-transitory computer readable medium of claim 15, wherein the imaging data is determined from one or more images of the cancer tumor and/or tumor-associated tissue damage.

17. The at least one non-transitory computer readable medium of claim 15, further comprising instructions, which when executed by the at least one processor cause the at least one processor to display subject-specific parameters of tumor growth dynamics, wherein the growth dynamics comprise motility, birth, and death dynamics of the cancer tumor.

18. The at least one non-transitory computer readable medium of claim 2, further comprising instructions, which when executed by the at least one processor cause the at least one processor to generate a report of the subject-specific parameters of tumor growth dynamics.

19. A computer-implemented method for estimating subject-specific parameters of growth dynamics of a cancer tumor in a subject having a cancer tumor, the method comprising:

a. providing a computer system having at least one processor and associated memory comprising an approximate wave profile of a traveling wave solution obtained using a reaction-diffusion model of tumor growth, the computer system comprising instructions to:

i. quantify measures of morphological features of the cancer tumor in the subject, the morphological features comprising a core, an invasive front, and tumor-associated tissue damage, and the measures comprising a volume of the core, a volume of the invasive front, and a volume of the tumor-associated tissue damage; and ii. estimating the subject-specific parameters by fitting an approximate wave profile of a traveling wave solution to a tumor profile derived from the quantified measures from i, wherein the approximate wave profile is generated using a reaction-diffusion model of tumor growth that incorporates a growth factor defined in terms of a proliferating cell density and a quiescent cell density of the cancer tumor, the traveling wave solution being defined in terms of the proliferating cell density and the quiescent cell density of the cancer tumor;

b. inputting the morphological measures of the cancer tumor in the subject;

c. processing the morphological measures to quantify the morphological measures of the cancer tumor in the subject;

d. processing the traveling solution profile of the reaction-diffusion model to fit the solution profile to the quantified measures; and e. computing the subject-specific parameters of growth dynamics of the cancer tumor from the fitted traveling solution profile.

\* \* \* \* \*